United States Patent
Nimkar et al.

(10) Patent No.: US 8,500,939 B2
(45) Date of Patent: Aug. 6, 2013

(54) MANUFACTURE OF SPLIT TIP CATHETERS

(75) Inventors: Shekhar D. Nimkar, Swampscott, MA (US); Christian Dufresne, Sr., Newton, MA (US); Eric Tobin, North Andover, MA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 573 days.

(21) Appl. No.: 12/244,514

(22) Filed: Oct. 2, 2008

(65) Prior Publication Data

US 2009/0204052 A1 Aug. 13, 2009

Related U.S. Application Data

(60) Provisional application No. 60/980,633, filed on Oct. 17, 2007.

(51) Int. Cl.
*B29C 65/02* (2006.01)
*B32B 37/00* (2006.01)
*B32B 38/00* (2006.01)

(52) U.S. Cl.
USPC ........ 156/257; 156/268; 156/308.2; 604/523; 604/908; 604/265; 604/43; 604/244; 128/898

(58) Field of Classification Search
USPC ........ 156/257, 268, 308.2; 606/908; 604/523, 604/265, 43, 266; 128/898, 912
See application file for complete search history.

(56) References Cited

U.S. PATENT DOCUMENTS

| | | | |
|---|---|---|---|
| 701,075 A | 5/1902 | McCully | |
| 1,696,018 A | 12/1928 | Scheliberg | |
| 1,856,811 A | 5/1932 | Inaki | |
| 2,024,982 A | 12/1935 | Scott | |
| 2,173,527 A | 9/1939 | Agayoff | |
| 2,286,462 A | 6/1942 | Chaffin | |
| 2,393,002 A | 1/1946 | Smith | |

(Continued)

FOREIGN PATENT DOCUMENTS

| | | |
|---|---|---|
| BE | 834211 | 2/1976 |
| CA | 1150122 | 7/1983 |

(Continued)

OTHER PUBLICATIONS

OriGen, "OriGen Biomedical Dual Lumen Catheter," http://origen.net/catheter.html, Copyright 2005, 4 pages.

(Continued)

*Primary Examiner* — Linda L Gray
(74) *Attorney, Agent, or Firm* — Rutan & Tucker, LLP

(57) ABSTRACT

Multi-lumen catheter devices having at least one split-tipped end are disclosed, together with methods of forming such split tip catheters. In one aspect of the invention, the manufacturing methods can include the steps of: providing a catheter body having at least a first and a second internal lumen extending longitudinally through the catheter body; removing a distal portion of the catheter body to form a first distal tip segment such that the first lumen extends longitudinally within this tip segment beyond the second lumen; and joining a second lumen tip segment to the catheter body in communication with the second lumen. The second tip segment can be joined to the catheter body such that it is at least partially separated from the first tip segment and, in some embodiments, preferably diverges at an angle relative to the first tip segment.

24 Claims, 10 Drawing Sheets

(56) References Cited

U.S. PATENT DOCUMENTS

| | | |
|---|---|---|
| 2,910,981 A | 11/1959 | Wilson et al. |
| 3,144,868 A | 8/1964 | Jascalevich |
| 3,176,690 A | 4/1965 | H'Doubler |
| 3,256,885 A | 6/1966 | Higgins et al. |
| 3,416,532 A | 12/1968 | Grossman |
| 3,426,759 A | 2/1969 | Smith |
| 3,460,255 A | 8/1969 | Hutson |
| D217,795 S | 6/1970 | Spaven |
| 3,612,038 A | 10/1971 | Halligan |
| 3,736,939 A | 6/1973 | Taylor |
| 3,805,794 A | 4/1974 | Schlesinger |
| 3,812,851 A | 5/1974 | Rodriguez |
| 3,848,604 A | 11/1974 | Sackner |
| 3,890,977 A | 6/1975 | Wilson |
| 3,929,126 A | 12/1975 | Corsaut |
| 3,935,857 A | 2/1976 | Co |
| 3,995,623 A | 12/1976 | Blake et al. |
| 4,068,659 A | 1/1978 | Moorehead |
| 4,072,146 A | 2/1978 | Howes |
| 4,072,153 A | 2/1978 | Swartz |
| 4,098,275 A | 7/1978 | Consalvo |
| 4,114,625 A | 9/1978 | Onat |
| 4,117,836 A | 10/1978 | Erikson |
| 4,129,129 A | 12/1978 | Amrine |
| 4,134,402 A | 1/1979 | Mahurkar |
| 4,149,535 A | 4/1979 | Volder et al. |
| 4,180,068 A | 12/1979 | Jacobsen et al. |
| 4,248,224 A | 2/1981 | Jones |
| 4,276,880 A | 7/1981 | Malmin |
| 4,292,976 A | 10/1981 | Banka |
| 4,299,228 A | 11/1981 | Peters |
| 4,300,550 A | 11/1981 | Gandi et al. |
| 4,309,994 A | 1/1982 | Grunwald |
| 4,327,722 A | 5/1982 | Groshong et al. |
| 4,385,631 A | 5/1983 | Uthmann |
| 4,392,855 A | 7/1983 | Oreopoulos et al. |
| 4,403,983 A | 9/1983 | Edelman et al. |
| 4,405,313 A | 9/1983 | Sisley et al. |
| 4,406,656 A | 9/1983 | Hattler et al. |
| D272,651 S | 2/1984 | Mahurkar |
| 4,431,426 A | 2/1984 | Groshong et al. |
| 4,432,722 A | 2/1984 | Bohan, Jr. et al. |
| 4,432,752 A | 2/1984 | Marlon |
| 4,445,893 A | 5/1984 | Bodicky |
| 4,451,252 A | 5/1984 | Martin |
| 4,453,928 A | 6/1984 | Steiger |
| 4,465,482 A | 8/1984 | Tittel et al. |
| 4,490,138 A | 12/1984 | Lipsky et al. |
| 4,493,696 A | 1/1985 | Uldall |
| RE31,873 E | 4/1985 | Howes |
| 4,531,933 A | 7/1985 | Norton et al. |
| 4,543,087 A | 9/1985 | Sommercorn et al. |
| 4,545,373 A | 10/1985 | Christoudias |
| 4,557,261 A | 12/1985 | Rugheimer et al. |
| 4,568,329 A | 2/1986 | Mahurkar |
| 4,568,338 A | 2/1986 | Todd |
| 4,573,476 A | 3/1986 | Ruiz |
| 4,581,012 A | 4/1986 | Brown et al. |
| 4,583,968 A | 4/1986 | Mahurkar |
| 4,583,986 A | 4/1986 | Lapidus |
| 4,601,697 A | 7/1986 | Mammolenti et al. |
| 4,619,643 A | 10/1986 | Bai |
| 4,623,327 A | 11/1986 | Mahurkar |
| 4,626,240 A | 12/1986 | Edelman et al. |
| 4,642,101 A | 2/1987 | Krolikowski et al. |
| 4,643,711 A | 2/1987 | Bates |
| 4,666,426 A | 5/1987 | Aigner et al. |
| 4,668,221 A | 5/1987 | Luther |
| 4,670,009 A | 6/1987 | Bullock |
| 4,675,004 A | 6/1987 | Hadford et al. |
| 4,681,122 A | 7/1987 | Winters et al. |
| 4,681,564 A | 7/1987 | Landreneau |
| 4,681,570 A | 7/1987 | Dalton |
| 4,682,978 A | 7/1987 | Martin |
| 4,687,471 A | 8/1987 | Twardowski et al. |
| 4,692,141 A | 9/1987 | Mahurkar |
| 4,694,838 A | 9/1987 | Wijayarthna et al. |
| 4,701,159 A | 10/1987 | Brown et al. |
| 4,702,917 A | 10/1987 | Schindler |
| 4,713,171 A | 12/1987 | Polaschegg |
| 4,717,379 A | 1/1988 | Ekholmer et al. |
| 4,735,620 A | 4/1988 | Ruiz |
| 4,737,141 A | 4/1988 | Spits |
| 4,737,152 A | 4/1988 | Alchas |
| 4,738,667 A | 4/1988 | Galloway |
| 4,748,808 A | 6/1988 | Hill |
| 4,755,176 A | 7/1988 | Patel |
| 4,769,016 A | 9/1988 | Labianca et al. |
| 4,770,652 A | 9/1988 | Mahurkar |
| 4,772,268 A | 9/1988 | Bates |
| 4,772,269 A | 9/1988 | Twardowski et al. |
| 4,776,841 A | 10/1988 | Catalano |
| 4,777,951 A | 10/1988 | Cribier et al. |
| 4,784,638 A | 11/1988 | Ghajar et al. |
| 4,790,809 A | 12/1988 | Kuntz |
| 4,795,439 A | 1/1989 | Guest |
| 4,801,297 A | 1/1989 | Mueller |
| 4,804,359 A | 2/1989 | Grunwald et al. |
| 4,808,155 A | 2/1989 | Mahurkar |
| 4,808,163 A | 2/1989 | Laub |
| 4,809,710 A | 3/1989 | Williamson |
| 4,820,265 A | 4/1989 | DeSatnick et al. |
| 4,832,687 A | 5/1989 | Smith, III |
| 4,834,709 A | 5/1989 | Banning et al. |
| 4,842,582 A | 6/1989 | Mahurkar |
| 4,842,592 A | 6/1989 | Caggiani et al. |
| 4,846,814 A | 7/1989 | Ruiz |
| 4,863,441 A | 9/1989 | Lindsay et al. |
| 4,867,742 A | 9/1989 | Calderon |
| 4,892,518 A | 1/1990 | Cupp et al. |
| 4,894,057 A | 1/1990 | Howes |
| 4,895,561 A | 1/1990 | Mahurkar |
| 4,898,591 A | 2/1990 | Jang et al. |
| 4,906,238 A | 3/1990 | Greenfeld et al. |
| 4,925,452 A | 5/1990 | Melinyshyn et al. |
| 4,927,418 A | 5/1990 | Dake et al. |
| 4,935,004 A | 6/1990 | Cruz |
| 4,935,010 A | 6/1990 | Cox et al. |
| 4,935,044 A | 6/1990 | Schoenpflug et al. |
| 4,936,826 A | 6/1990 | Amarasinghe |
| 4,950,232 A | 8/1990 | Ruzicka et al. |
| 4,950,259 A | 8/1990 | Geary et al. |
| 4,951,665 A | 8/1990 | Schneider |
| 4,961,729 A | 10/1990 | Vaillancourt |
| 4,961,731 A | 10/1990 | Bodicky et al. |
| 4,961,809 A | 10/1990 | Martin et al. |
| 4,968,307 A | 11/1990 | Dake et al. |
| 4,969,890 A | 11/1990 | Sugita et al. |
| 4,981,477 A | 1/1991 | Schon et al. |
| 4,985,014 A | 1/1991 | Orejola |
| 4,990,138 A | 2/1991 | Bacich et al. |
| 4,994,027 A | 2/1991 | Farrell |
| 4,995,865 A | 2/1991 | Gahara et al. |
| 5,009,636 A | 4/1991 | Wortley et al. |
| 5,015,230 A | 5/1991 | Martin et al. |
| 5,016,640 A | 5/1991 | Ruiz |
| 5,021,044 A | 6/1991 | Sharkawy |
| 5,041,101 A | 8/1991 | Seder et al. |
| 5,041,107 A | 8/1991 | Heil, Jr. |
| 5,049,138 A | 9/1991 | Chevalier et al. |
| 5,053,003 A | 10/1991 | Dadson et al. |
| 5,053,004 A | 10/1991 | Markel et al. |
| 5,053,023 A | 10/1991 | Martin |
| 5,057,073 A | 10/1991 | Martin |
| 5,059,170 A | 10/1991 | Cameron |
| 5,069,673 A | 12/1991 | Shwab |
| 5,074,841 A | 12/1991 | Ademovic et al. |
| 5,084,013 A | 1/1992 | Takase et al. |
| 5,098,412 A | 3/1992 | Shiu |
| 5,100,395 A | 3/1992 | Rosenberg |
| 5,102,402 A * | 4/1992 | Dror et al. ............ 604/265 |
| 5,106,368 A | 4/1992 | Uldall et al. |
| 5,106,376 A | 4/1992 | Mononen et al. |
| 5,111,829 A | 5/1992 | Alvarez de Toledo |

| | | | | | |
|---|---|---|---|---|---|
| 5,112,301 A | 5/1992 | Fenton, Jr. et al. | 5,451,206 A | 9/1995 | Young |
| 5,114,423 A | 5/1992 | Kasprzyk et al. | 5,451,233 A | 9/1995 | Yock |
| 5,117,836 A | 6/1992 | Millar | 5,458,570 A | 10/1995 | May, Jr. |
| 5,120,299 A | 6/1992 | Lombardi | 5,458,582 A | 10/1995 | Nakao |
| 5,120,304 A | 6/1992 | Sasaki | 5,472,417 A | 12/1995 | Martin et al. |
| 5,122,125 A | 6/1992 | Deuss et al. | 5,472,432 A | 12/1995 | Martin |
| 5,125,904 A | 6/1992 | Lee | 5,476,453 A | 12/1995 | Mehta |
| 5,129,891 A | 7/1992 | Young | 5,480,380 A | 1/1996 | Martin |
| 5,135,599 A | 8/1992 | Martin et al. | 5,486,159 A | 1/1996 | Mahurkar |
| 5,139,486 A | 8/1992 | Moss | 5,489,278 A | 2/1996 | Abrahamson |
| 5,156,592 A | 10/1992 | Martin et al. | 5,496,292 A | 3/1996 | Burnham |
| 5,163,928 A | 11/1992 | Hobbs et al. | 5,505,710 A | 4/1996 | Dorsey, III |
| 5,167,623 A | 12/1992 | Cianci et al. | 5,507,723 A | 4/1996 | Keshaviah |
| 5,171,216 A | 12/1992 | Dasse et al. | 5,509,897 A | 4/1996 | Twardowski et al. |
| 5,171,227 A | 12/1992 | Twardowski et al. | 5,509,900 A | 4/1996 | Kirkman |
| 5,178,616 A * | 1/1993 | Uemiya et al. .................. 606/7 | 5,509,902 A | 4/1996 | Raulerson |
| 5,188,592 A | 2/1993 | Hakki | 5,542,925 A | 8/1996 | Orth |
| 5,188,593 A | 2/1993 | Martin | 5,545,373 A | 8/1996 | Maziasz et al. |
| 5,190,520 A | 3/1993 | Fenton, Jr. et al. | 5,556,390 A | 9/1996 | Hicks |
| 5,190,529 A | 3/1993 | McCrory et al. | 5,556,930 A | 9/1996 | Brehm et al. |
| 5,191,898 A | 3/1993 | Millar | 5,558,635 A | 9/1996 | Cannon |
| 5,195,962 A | 3/1993 | Martin et al. | 5,562,609 A | 10/1996 | Brumbach |
| 5,197,951 A | 3/1993 | Mahurkar | 5,569,182 A | 10/1996 | Twardowski et al. |
| 5,197,973 A | 3/1993 | Pang et al. | 5,569,195 A | 10/1996 | Saab |
| 5,197,976 A | 3/1993 | Herweck et al. | 5,571,093 A | 11/1996 | Cruz et al. |
| 5,201,723 A | 4/1993 | Quinn | 5,584,803 A | 12/1996 | Stevens et al. |
| 5,207,648 A | 5/1993 | Gross | 5,599,304 A | 2/1997 | Shaari |
| 5,207,650 A | 5/1993 | Martin | 5,599,328 A | 2/1997 | Stevens |
| 5,209,723 A | 5/1993 | Twardowski et al. | 5,607,462 A | 3/1997 | Imran |
| 5,209,725 A | 5/1993 | Roth | 5,624,392 A | 4/1997 | Saab |
| 5,209,742 A | 5/1993 | Venema et al. | 5,624,413 A | 4/1997 | Markel et al. |
| 5,211,256 A | 5/1993 | Muramatsu | 5,632,729 A | 5/1997 | Cai et al. |
| 5,215,527 A | 6/1993 | Beck et al. | 5,637,102 A | 6/1997 | Tolkoff et al. |
| 5,221,255 A | 6/1993 | Mahurkar et al. | 5,642,270 A | 6/1997 | Green et al. |
| 5,221,256 A | 6/1993 | Mahurkar | 5,662,606 A | 9/1997 | Cimino et al. |
| 5,222,949 A | 6/1993 | Kaldany | 5,665,067 A | 9/1997 | Linder et al. |
| 5,226,880 A | 7/1993 | Martin et al. | 5,685,867 A | 11/1997 | Twardowski et al. |
| 5,234,438 A | 8/1993 | Semrad | 5,686,867 A | 11/1997 | Sutardja et al. |
| 5,236,016 A | 8/1993 | Vogelsang et al. | 5,693,030 A | 12/1997 | Lee et al. |
| 5,242,398 A | 9/1993 | Knoll et al. | 5,695,457 A | 12/1997 | St. Goar et al. |
| 5,246,430 A | 9/1993 | MacFarlane | 5,704,915 A | 1/1998 | Melsky et al. |
| 5,250,034 A | 10/1993 | Appling et al. | 5,713,849 A | 2/1998 | Bosma et al. |
| 5,254,084 A | 10/1993 | Geary | 5,713,853 A | 2/1998 | Clark et al. |
| 5,273,527 A | 12/1993 | Schatz et al. | 5,717,216 A | 2/1998 | McCoy et al. |
| 5,273,534 A | 12/1993 | Knoepfler | 5,718,678 A | 2/1998 | Fleming, III |
| 5,279,596 A | 1/1994 | Castaneda et al. | 5,718,692 A | 2/1998 | Schon et al. |
| 5,279,599 A | 1/1994 | Wilk | 5,720,735 A | 2/1998 | Dorros |
| 5,306,240 A | 4/1994 | Berry | 5,738,649 A | 4/1998 | Macoviak |
| 5,312,337 A | 5/1994 | Flaherty et al. | 5,741,329 A | 4/1998 | Agrawal et al. |
| 5,312,357 A | 5/1994 | Buijs et al. | 5,743,873 A | 4/1998 | Cai et al. |
| 5,318,517 A | 6/1994 | Reiman | 5,752,939 A | 5/1998 | Makoto et al. |
| 5,322,519 A | 6/1994 | Ash | 5,769,796 A | 6/1998 | Palermo et al. |
| 5,324,274 A | 6/1994 | Martin | 5,772,643 A | 6/1998 | Howell et al. |
| 5,338,308 A | 8/1994 | Wilk | 5,776,096 A | 7/1998 | Fields |
| 5,342,295 A | 8/1994 | Imran | 5,776,111 A | 7/1998 | Tesio |
| 5,342,386 A | 8/1994 | Trotta | 5,785,686 A | 7/1998 | Runge |
| 5,346,471 A | 9/1994 | Raulerson | 5,792,094 A | 8/1998 | Stevens et al. |
| 5,348,536 A | 9/1994 | Young et al. | 5,792,123 A | 8/1998 | Ensminger |
| 5,350,358 A | 9/1994 | Martin | 5,797,869 A | 8/1998 | Martin et al. |
| 5,360,397 A | 11/1994 | Pinchuk | 5,800,384 A | 9/1998 | Russell et al. |
| 5,360,407 A | 11/1994 | Leonard et al. | 5,800,414 A | 9/1998 | Cazal et al. |
| 5,364,344 A | 11/1994 | Beattie et al. | 5,800,516 A | 9/1998 | Fine et al. |
| 5,374,245 A | 12/1994 | Mahurkar | 5,807,311 A | 9/1998 | Palestrant |
| 5,378,230 A | 1/1995 | Mahurkar | 5,807,318 A | 9/1998 | St. Goar et al. |
| 5,380,276 A | 1/1995 | Miller et al. | 5,807,329 A | 9/1998 | Gelman |
| 5,380,290 A | 1/1995 | Makower et al. | 5,809,897 A | 9/1998 | Powell et al. |
| 5,382,238 A | 1/1995 | Abrahamson et al. | 5,810,789 A | 9/1998 | Powers et al. |
| 5,389,087 A * | 2/1995 | Miraki .......................... 604/247 | 5,814,016 A | 9/1998 | Valley et al. |
| 5,389,090 A | 2/1995 | Fischell et al. | 5,830,184 A | 11/1998 | Basta |
| 5,395,316 A | 3/1995 | Martin et al. | 5,830,196 A | 11/1998 | Hicks |
| 5,399,168 A | 3/1995 | Wadsworth, Jr. et al. | 5,833,671 A | 11/1998 | Macoviak et al. |
| 5,403,291 A | 4/1995 | Abrahamson | 5,858,009 A | 1/1999 | Jonkman |
| 5,405,320 A | 4/1995 | Twardowski et al. | 5,861,010 A | 1/1999 | Boussignac et al. |
| 5,405,341 A | 4/1995 | Martin | 5,868,717 A | 2/1999 | Prosl |
| 5,409,463 A | 4/1995 | Thomas et al. | 5,873,865 A | 2/1999 | Horzewski et al. |
| 5,417,668 A | 5/1995 | Setzer et al. | 5,876,366 A | 3/1999 | Dykstra et al. |
| 5,423,768 A | 6/1995 | Folden et al. | 5,876,426 A | 3/1999 | Kume et al. |
| 5,431,661 A | 7/1995 | Koch | 5,882,347 A | 3/1999 | Mouris-Laan et al. |
| 5,451,026 A | 9/1995 | Smith | 5,891,111 A | 4/1999 | Ismael et al. |

| Patent | Kind | Date | Inventor |
|---|---|---|---|
| 5,904,670 | A | 5/1999 | Schreiner |
| 5,911,715 | A | 6/1999 | Berg et al. |
| 5,913,848 | A | 6/1999 | Luther et al. |
| 5,916,208 | A | 6/1999 | Luther et al. |
| 5,919,160 | A | 7/1999 | Sanfilippo, II |
| 5,944,732 | A | 8/1999 | Raulerson et al. |
| 5,947,937 | A | 9/1999 | Urrutia et al. |
| 5,947,953 | A | 9/1999 | Ash et al. |
| 5,957,879 | A | 9/1999 | Roberts et al. |
| 5,957,893 | A | 9/1999 | Luther et al. |
| 5,957,912 | A | 9/1999 | Heitzmann |
| 5,961,486 | A | 10/1999 | Twardowski et al. |
| 5,964,796 | A | 10/1999 | Imran |
| 5,976,103 | A | 11/1999 | Martin |
| 5,976,120 | A | 11/1999 | Chow et al. |
| 5,980,551 | A | 11/1999 | Summers et al. |
| 5,984,908 | A | 11/1999 | Davis et al. |
| 5,989,206 | A | 11/1999 | Prosl et al. |
| 5,989,213 | A | 11/1999 | Maginot |
| 6,001,079 | A | 12/1999 | Pourchez |
| 6,033,382 | A | 3/2000 | Basta |
| 6,036,654 | A | 3/2000 | Quinn et al. |
| 6,059,771 | A | 5/2000 | Balbierz et al. |
| 6,074,374 | A | 6/2000 | Fulton |
| 6,086,555 | A | 7/2000 | Eliasen et al. |
| 6,090,096 | A | 7/2000 | St. Goar et al. |
| 6,099,513 | A | 8/2000 | Spehalski |
| 6,103,778 | A | 8/2000 | Hyon et al. |
| 6,106,540 | A | 8/2000 | White et al. |
| 6,113,572 | A | 9/2000 | Gailey et al. |
| 6,117,117 | A | 9/2000 | Mauch |
| 6,120,494 | A | 9/2000 | Jonkman |
| 6,126,631 | A | 10/2000 | Loggie |
| 6,146,354 | A | 11/2000 | Beil |
| 6,146,373 | A | 11/2000 | Cragg et al. |
| 6,152,909 | A | 11/2000 | Bagaoisan et al. |
| 6,156,016 | A | 12/2000 | Maginot |
| 6,161,547 | A | 12/2000 | Barbut |
| 6,178,356 | B1 | 1/2001 | Chastain et al. |
| 6,180,059 | B1 | 1/2001 | Divino, Jr. et al. |
| 6,190,349 | B1 | 2/2001 | Ash et al. |
| 6,190,371 | B1 | 2/2001 | Maginot et al. |
| 6,193,685 | B1 | 2/2001 | Goodin |
| 6,196,996 | B1 | 3/2001 | Teirstein |
| 6,206,849 | B1 | 3/2001 | Martin et al. |
| 6,210,365 | B1 | 4/2001 | Afzal |
| 6,210,380 | B1 | 4/2001 | Mauch |
| 6,217,527 | B1 | 4/2001 | Selmon et al. |
| 6,224,622 | B1 | 5/2001 | Kotzev |
| 6,238,406 | B1 | 5/2001 | Ellis et al. |
| 6,264,627 | B1 | 7/2001 | Liska et al. |
| 6,273,879 | B1 | 8/2001 | Keith et al. |
| 6,280,423 | B1 | 8/2001 | Davey et al. |
| 6,287,326 | B1 | 9/2001 | Pecor |
| 6,293,927 | B1 | 9/2001 | McGuckin, Jr. |
| 6,293,958 | B1 | 9/2001 | Berry et al. |
| 6,296,631 | B2 | 10/2001 | Chow |
| 6,299,631 | B1 | 10/2001 | Shalaby |
| 6,322,551 | B1 | 11/2001 | Brugger |
| 6,328,730 | B1 | 12/2001 | Harkrider, Jr. |
| 6,342,120 | B1 | 1/2002 | Basta |
| 6,361,529 | B1 | 3/2002 | Goodin et al. |
| 6,383,172 | B1 | 5/2002 | Barbut |
| 6,394,141 | B2 | 5/2002 | Wages et al. |
| 6,394,142 | B1 | 5/2002 | Woelfel et al. |
| 6,409,700 | B1 | 6/2002 | Siegel, Jr. et al. |
| 6,413,228 | B1 | 7/2002 | Hung et al. |
| 6,428,513 | B1 | 8/2002 | Abrahamson |
| 6,443,922 | B1 | 9/2002 | Roberts et al. |
| 6,450,988 | B1 | 9/2002 | Bradshaw |
| 6,453,185 | B1 | 9/2002 | O'Keefe |
| 6,454,997 | B1 | 9/2002 | Divino, Jr. et al. |
| 6,463,335 | B1 | 10/2002 | Munch et al. |
| 6,475,207 | B1 | 11/2002 | Maginot et al. |
| 6,475,209 | B1 | 11/2002 | Larson et al. |
| 6,478,789 | B1 | 11/2002 | Spehalski et al. |
| 6,482,169 | B1 | 11/2002 | Kuhle |
| 6,533,763 | B1 | 3/2003 | Schneiter |
| 6,565,594 | B1 | 5/2003 | Herweck et al. |
| 6,576,001 | B2 | 6/2003 | Werneth et al. |
| 6,582,459 | B1 | 6/2003 | Lau et al. |
| 6,585,705 | B1 | 7/2003 | Maginot et al. |
| 6,592,565 | B2 | 7/2003 | Twardowski |
| 6,595,966 | B2 | 7/2003 | Davey et al. |
| 6,620,118 | B1 | 9/2003 | Prosl et al. |
| 6,638,242 | B2 | 10/2003 | Wilson et al. |
| 6,659,134 | B2 | 12/2003 | Navis |
| 6,682,498 | B2 | 1/2004 | Ross |
| 6,682,519 | B1 | 1/2004 | Schon |
| 6,695,832 | B2 | 2/2004 | Schon et al. |
| 6,702,776 | B2 | 3/2004 | Quinn |
| 6,712,797 | B1 | 3/2004 | Southern, Jr. |
| 6,712,798 | B2 | 3/2004 | Constantz |
| 6,719,717 | B1 | 4/2004 | Johnson et al. |
| 6,719,749 | B1 | 4/2004 | Schweikert et al. |
| 6,723,084 | B1 | 4/2004 | Maginot et al. |
| 6,723,114 | B2 | 4/2004 | Shalaby |
| 6,730,299 | B1 | 5/2004 | Tayot et al. |
| 6,752,827 | B2 | 6/2004 | Ross et al. |
| 6,755,851 | B2 | 6/2004 | Noda et al. |
| 6,758,836 | B2 | 7/2004 | Zawacki |
| 6,786,664 | B2 | 9/2004 | Claramunt et al. |
| 6,786,884 | B1 | 9/2004 | DeCant, Jr. et al. |
| 6,796,991 | B2 | 9/2004 | Nardeo |
| 6,797,107 | B1 | 9/2004 | Kotzey |
| 6,808,510 | B1 | 10/2004 | DiFiore |
| 6,814,718 | B2 | 11/2004 | McGuckin, Jr. et al. |
| 6,819,951 | B2 | 11/2004 | Patel et al. |
| 6,821,287 | B1 | 11/2004 | Jang |
| 6,824,554 | B1 | 11/2004 | Jang |
| 6,835,452 | B1 | 12/2004 | Hamerski |
| 6,837,864 | B1 | 1/2005 | Bertolero et al. |
| 6,852,079 | B2 | 2/2005 | Miyano |
| 6,852,097 | B1 | 2/2005 | Fulton, III |
| 6,858,019 | B2 | 2/2005 | McGuckin, Jr. et al. |
| 6,872,198 | B1 | 3/2005 | Wilson et al. |
| 6,878,143 | B2 | 4/2005 | Andersen |
| 6,881,211 | B2 | 4/2005 | Schweikert et al. |
| 6,911,014 | B2 | 6/2005 | Wentling et al. |
| 6,913,601 | B2 | 7/2005 | St. Goar et al. |
| 6,916,313 | B2 | 7/2005 | Cunningham |
| 6,921,396 | B1 | 7/2005 | Wilson et al. |
| 6,921,411 | B2 | 7/2005 | Yock |
| 6,934,142 | B2 | 8/2005 | Grosse et al. |
| 6,966,886 | B2 | 11/2005 | Appling |
| 6,969,381 | B2 | 11/2005 | Voorhees |
| 6,991,625 | B1 | 1/2006 | Gately et al. |
| D515,211 | S | 2/2006 | Chesnin |
| 6,997,894 | B2 | 2/2006 | Caresio |
| 7,008,395 | B1 | 3/2006 | Loggie |
| 7,011,645 | B2 | 3/2006 | McGuckin, Jr. et al. |
| 7,018,384 | B2 | 3/2006 | Skakoon |
| 7,029,467 | B2 | 4/2006 | Currier et al. |
| 7,066,914 | B2 | 6/2006 | Andersen |
| 7,066,925 | B2 | 6/2006 | Gately et al. |
| 7,074,213 | B2 | 7/2006 | McGuckin, Jr. et al. |
| 7,077,829 | B2 | 7/2006 | McGuckin, Jr. et al. |
| 7,087,053 | B2 | 8/2006 | Vanney |
| 7,090,654 | B2 | 8/2006 | Lotito et al. |
| 7,108,674 | B2 | 9/2006 | Quinn |
| D530,420 | S | 10/2006 | Chesnin |
| 7,128,734 | B1 | 10/2006 | Wilson et al. |
| 7,130,700 | B2 | 10/2006 | Gardeski et al. |
| 7,141,035 | B2 | 11/2006 | Haggstrom |
| RE39,451 | E | 12/2006 | Kuhle |
| 7,182,746 | B2 | 2/2007 | Haarala et al. |
| 7,300,430 | B2 | 11/2007 | Wilson et al. |
| 7,322,953 | B2 | 1/2008 | Redinger |
| 7,347,852 | B2 | 3/2008 | Hobbs et al. |
| 7,381,204 | B2 | 6/2008 | Wilson et al. |
| 7,393,339 | B2 | 7/2008 | Zawacki |
| 7,422,571 | B2 | 9/2008 | Schweikert et al. |
| 7,465,286 | B2 | 12/2008 | Patterson et al. |
| 7,485,107 | B2 | 2/2009 | DiFiore et al. |
| 7,569,029 | B2 | 8/2009 | Clark |
| 7,575,563 | B2 | 8/2009 | Appling |
| 7,798,999 | B2 | 9/2010 | Bailey et al. |
| 8,021,321 | B2 | 9/2011 | Zawacki |

| | | |
|---|---|---|
| 8,066,660 B2 | 11/2011 | Gregersen et al. |
| 8,092,415 B2 | 1/2012 | Moehle |
| 8,152,951 B2 * | 4/2012 | Zawacki et al. ............ 156/290 |
| 8,206,371 B2 | 6/2012 | Nimkar et al. |
| 8,292,841 B2 | 10/2012 | Gregersen |
| 2001/0041857 A1 | 11/2001 | Sansoucy |
| 2001/0041873 A1 | 11/2001 | Dopper et al. |
| 2002/0013569 A1 | 1/2002 | Sterman et al. |
| 2002/0026156 A1 | 2/2002 | Quinn |
| 2002/0086047 A1 | 7/2002 | Mueller et al. |
| 2002/0087108 A1 | 7/2002 | Maginot et al. |
| 2002/0087145 A1 | 7/2002 | Ehwald et al. |
| 2002/0091362 A1 | 7/2002 | Maginot et al. |
| 2002/0091430 A1 | 7/2002 | Dobak et al. |
| 2002/0099326 A1 | 7/2002 | Wilson et al. |
| 2002/0099327 A1 | 7/2002 | Wilson et al. |
| 2002/0107506 A1 | 8/2002 | McGuckin et al. |
| 2002/0138031 A1 | 9/2002 | Ross |
| 2002/0169490 A1 | 11/2002 | Noda et al. |
| 2002/0177904 A1 | 11/2002 | Huxel et al. |
| 2003/0023198 A1 | 1/2003 | Twardowski |
| 2003/0088213 A1 | 5/2003 | Schweikert et al. |
| 2003/0093027 A1 | 5/2003 | McGuckin et al. |
| 2003/0097091 A1 | 5/2003 | Hobbs et al. |
| 2003/0144623 A1 | 7/2003 | Heath et al. |
| 2003/0149395 A1 | 8/2003 | Zawacki |
| 2003/0153898 A1 | 8/2003 | Schon et al. |
| 2003/0187411 A1 | 10/2003 | Constantz |
| 2003/0204179 A1 | 10/2003 | Davey et al. |
| 2004/0054321 A1 | 3/2004 | Schon et al. |
| 2004/0059314 A1 | 3/2004 | Schon et al. |
| 2004/0064086 A1 | 4/2004 | Gottlieb et al. |
| 2004/0065333 A1 | 4/2004 | Wilson et al. |
| 2004/0075198 A1 | 4/2004 | Schweikert et al. |
| 2004/0087892 A1 | 5/2004 | Cunningham |
| 2004/0092863 A1 | 5/2004 | Raulerson et al. |
| 2004/0097863 A1 | 5/2004 | Appling |
| 2004/0097903 A1 | 5/2004 | Raulerson |
| 2004/0122418 A1 | 6/2004 | Voorhees |
| 2004/0147903 A1 | 7/2004 | Latini |
| 2004/0167463 A1 | 8/2004 | Zawacki et al. |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0193102 A1 | 9/2004 | Haggstrom |
| 2004/0210180 A1 | 10/2004 | Altman |
| 2004/0210187 A1 | 10/2004 | Zawacki |
| 2004/0210237 A1 | 10/2004 | Ross et al. |
| 2004/0220550 A1 | 11/2004 | Schryver |
| 2004/0230204 A1 | 11/2004 | Wortley et al. |
| 2004/0243095 A1 | 12/2004 | Nimkar et al. |
| 2004/0249337 A1 | 12/2004 | DiFiore |
| 2005/0003322 A1 | 1/2005 | Logan et al. |
| 2005/0004504 A1 | 1/2005 | Frye et al. |
| 2005/0013341 A1 | 1/2005 | Baghai |
| 2005/0025641 A1 | 2/2005 | Shibata et al. |
| 2005/0027282 A1 | 2/2005 | Schweikert et al. |
| 2005/0027289 A1 | 2/2005 | Castellano et al. |
| 2005/0033222 A1 | 2/2005 | Haggstrom et al. |
| 2005/0054989 A1 | 3/2005 | McGuckin et al. |
| 2005/0055012 A1 | 3/2005 | Trerotola |
| 2005/0059925 A1 | 3/2005 | Maginot et al. |
| 2005/0070842 A1 | 3/2005 | Lotito et al. |
| 2005/0080398 A1 | 4/2005 | Markel et al. |
| 2005/0085765 A1 | 4/2005 | Voorhees |
| 2005/0096585 A1 | 5/2005 | Schon et al. |
| 2005/0113904 A1 | 5/2005 | Shank et al. |
| 2005/0131341 A1 | 6/2005 | McGuckin et al. |
| 2005/0171469 A1 | 8/2005 | Cunningham |
| 2005/0187535 A1 | 8/2005 | Wilson et al. |
| 2005/0228339 A1 | 10/2005 | Clark |
| 2005/0245900 A1 | 11/2005 | Ash |
| 2005/0256461 A1 | 11/2005 | DiFiore et al. |
| 2005/0261663 A1 | 11/2005 | Patterson et al. |
| 2005/0267400 A1 | 12/2005 | Haarala et al. |
| 2005/0277862 A1 | 12/2005 | Anand |
| 2005/0288623 A1 | 12/2005 | Hjalmarsson |
| 2005/0288706 A1 | 12/2005 | Widomski et al. |
| 2006/0004316 A1 | 1/2006 | Difiore et al. |
| 2006/0004325 A1 | 1/2006 | Hamatake et al. |
| 2006/0009783 A1 | 1/2006 | Rome et al. |
| 2006/0015072 A1 | 1/2006 | Raulerson |
| 2006/0015130 A1 | 1/2006 | Voorhees et al. |
| 2006/0030827 A1 | 2/2006 | Raulerson et al. |
| 2006/0047267 A1 | 3/2006 | Gately et al. |
| 2006/0047268 A1 | 3/2006 | Stephens |
| 2006/0058775 A1 | 3/2006 | Stevens et al. |
| 2006/0064072 A1 | 3/2006 | Gately et al. |
| 2006/0095062 A1 | 5/2006 | Stephens |
| 2006/0100572 A1 | 5/2006 | DiMatteo et al. |
| 2006/0161100 A1 | 7/2006 | Hamboly |
| 2006/0184142 A1 | 8/2006 | Schon et al. |
| 2006/0189922 A1 | 8/2006 | Amarasinghe et al. |
| 2006/0206094 A1 | 9/2006 | Chesnin et al. |
| 2006/0251612 A1 | 11/2006 | Kotzev et al. |
| 2006/0253063 A1 | 11/2006 | Schweikert |
| 2006/0271012 A1 | 11/2006 | Canaud et al. |
| 2007/0005003 A1 | 1/2007 | Patterson et al. |
| 2007/0066964 A1 | 3/2007 | Atkins |
| 2007/0078478 A1 | 4/2007 | Atkins et al. |
| 2007/0106206 A1 | 5/2007 | Appling |
| 2007/0129704 A1 | 6/2007 | O'Mahony et al. |
| 2007/0167925 A1 | 7/2007 | Jacqmein |
| 2007/0225661 A1 | 9/2007 | Ash et al. |
| 2007/0225682 A1 | 9/2007 | Ash et al. |
| 2007/0282274 A1 | 12/2007 | Chesnin |
| 2008/0021417 A1 | 1/2008 | Zawacki et al. |
| 2008/0039774 A1 | 2/2008 | Zawacki et al. |
| 2008/0082079 A1 | 4/2008 | Braga et al. |
| 2008/0082080 A1 | 4/2008 | Braga |
| 2008/0097409 A1 | 4/2008 | Stephens |
| 2008/0214980 A1 | 9/2008 | Anand |
| 2008/0214992 A1 | 9/2008 | Haarala et al. |
| 2009/0112153 A1 | 4/2009 | Gregersen et al. |
| 2009/0118661 A1 | 5/2009 | Moehle et al. |
| 2009/0118701 A1 | 5/2009 | Nimkar et al. |
| 2009/0118707 A1 | 5/2009 | Schweikert et al. |
| 2009/0192435 A1 | 7/2009 | Gregersen |
| 2009/0204079 A1 | 8/2009 | Nimkar et al. |
| 2009/0205189 A1 | 8/2009 | Nimkar et al. |
| 2009/0209940 A1 | 8/2009 | Nimkar et al. |
| 2010/0331780 A1 | 12/2010 | Bellisario et al. |
| 2011/0020418 A1 | 1/2011 | Bosley, Jr. et al. |
| 2012/0059304 A1 | 3/2012 | Gregersen et al. |
| 2012/0089070 A1 | 4/2012 | Moehle et al. |
| 2012/0203206 A1 | 8/2012 | Nimkar et al. |

FOREIGN PATENT DOCUMENTS

| | | |
|---|---|---|
| CA | 2474351 A1 | 8/2003 |
| CN | 2788836 Y | 6/2006 |
| DE | 8815869 | 3/1989 |
| DE | 9108132 | 6/1991 |
| DE | 102005051211 A1 | 5/2007 |
| EP | 0030854 A2 | 6/1981 |
| EP | 0132344 A2 | 1/1985 |
| EP | 0301854 | 2/1989 |
| EP | 0332366 A2 | 9/1989 |
| EP | 0386408 A1 | 9/1990 |
| EP | 0453234 | 10/1991 |
| EP | 0476796 A1 | 3/1992 |
| EP | 0495263 A1 | 7/1992 |
| EP | 0 650 740 * | 5/1995 |
| EP | 0711574 A1 | 5/1996 |
| EP | 1471966 A1 | 11/2004 |
| EP | 1599247 A2 | 11/2005 |
| GB | 1503469 | 3/1978 |
| JP | 56-136569 A | 10/1981 |
| JP | 8-510935 T | 11/1996 |
| JP | 201137350 | 5/2001 |
| JP | 2008500081 A | 1/2008 |
| JP | 4827377 B2 | 11/2011 |
| MX | 249060 | 9/2007 |
| SU | 459237 A1 | 2/1975 |
| SU | 45923 A | 11/2004 |
| WO | 9108132 A1 | 6/1991 |
| WO | WO-9316741 A1 | 9/1993 |
| WO | WO-9316752 A1 | 9/1993 |
| WO | 9709086 A1 | 3/1997 |

| | | |
|---|---|---|
| WO | 9717102 | 5/1997 |
| WO | WO-9722374 A1 | 6/1997 |
| WO | 9737699 | 10/1997 |
| WO | 9904844 A1 | 2/1999 |
| WO | 0023137 A1 | 4/2000 |
| WO | 02058776 A2 | 8/2002 |
| WO | 02083223 A1 | 10/2002 |
| WO | 03030960 A2 | 4/2003 |
| WO | 03033049 A2 | 4/2003 |
| WO | 03066148 A1 | 8/2003 |
| WO | 2004075962 A2 | 9/2004 |
| WO | 2004096334 | 11/2004 |
| WO | 2004112876 | 12/2004 |
| WO | WO-2005018712 A2 | 3/2005 |
| WO | WO-2005023336 A2 | 3/2005 |
| WO | 2005077449 | 8/2005 |
| WO | 2005084741 A1 | 9/2005 |
| WO | 2005118039 A1 | 12/2005 |
| WO | 2006034877 | 4/2006 |
| WO | 2009051967 A1 | 4/2009 |
| WO | 2009055332 A1 | 4/2009 |

OTHER PUBLICATIONS

International Search Report & Written Opinion, PCT/US2008/078551, Issued Mar. 13, 2009, 12 pages.
International Search Report & Written Opinion, PCT/US2008/078560, Issued Mar. 16, 2009, 11 pages.
International Search Report & Written Opinion, PCT/US2008/078566, Issued Mar. 19, 2009, 11 pages.
International Search Report & Written Opinion, PCT/US2008/078571 Issued Mar. 16, 2009, 12 pages.
U.S. Appl. No. 12/244,544, filed Oct. 2, 2008, Fusion Manufacture of Multi-Lumen Catheters.
U.S. Appl. No. 12/244,554, filed Oct. 2, 2008, Catheters with Enlarged Arterial Lumens.
U.S. Appl. No. 12/244,559, filed Oct. 2, 2008, Manufacture of Fixed Tip Catheters.
Arrow Cannon II Plus brochure (2006).
Bander, et al., Central Venous Angioaccess for Hemodialysis and Its Complications, Seminars in Dialysis, 1992, vol. 5, No. 2, pp. 121-128.
Baranowski, L., Central Venous Access Devises, Journal of Intravenous Nursing, 1993, vol. 16, No. 3, pp. 167-194.
Believed to be an unpublished sketch of a conception by Dr. John Frusha; date of sketch believed to be Jun. 24, 1997.
Berkoben, et al., Maintenance of Permanent Hemodialysis Vascular Access Patency, ANNA Journal, 1995, vol. 22, No. 1, pp. 17-24.
Bolz, et al., Catheter Malfunction and Thrombus Formation on Double-Lumen Hemodialysis Catheters: An Intravascular Ultrasonographic Study, American Journal of Kidney Diseases, 1995, vol. 25, No. 4, pp. 597-602.
Bour, et al., Experience With the Double Lumen Silastic® Catheter for Hemoaccess Surgery, Gynecology & Obstetrics, 1990, vol. 171, pp. 33-39.
Campbell, et al., Radiological Insertion of Long-term Venous Access Devises, Seminars in Interventional Radiology, 1994, vol. 11, No. 4. pp. 366-375.
Canaud, B. et al., "Permanent Twin Catheter: a Vascular Access Option of Choice for Haemodialysis in Elderly Patients," 13(7):82-88 (1998).
Claim Construction Order of Federal District Court dated May 9, 2005 in *Thierry Pourchez and Bard Access Systems, Inc. v. Diatek, Inc. and Arrow International, Inc.* litigation (S.D. N.Y. 03 Civ. 0972).
Claim Construction Order of Federal District Court dated Oct. 31, 2006 in *Arrow Int'l. Inc. and Arrow Int'l. Investment Corp. v. Spire Biomedical, Inc.* litigation, (D. Mass. Civil Action No. 06-CV-11564).
Decision of Federal District Court dated Jul. 7, 2009 granting Summary Judgment of Invalidity in *Arrow Int'l. Inc. and Arrow Int'l. Investment Corp. v. Spire Biomedical, Inc.* litigation, (D. Mass. Civil Action No. 06-CV-11564).
Dialysis Vascular Access, Technological Innovations Improving Flow(AngioDynamics Inc.) brochure, 4 pages.

Donaldson, et al., Peripherally Inserted Central Venous Catheters: US-guided Vascular Access in Pediatric Patients1, Radiology, 1995, vol. 197, pp. 542-544.
Dunea, et al., A Survey of Permanent Double Lumen Catheters in Hemodialysis Patients, ASAIO Transac. 1991:37:M276-7.
Dupont et al., "Long-Term Development of Permcath Quinton Catheter" [French] Néphrologie 15: 105-10 (1994).
Gallichio, et al., Placement of a Double Lumen Silastic Catheter for Hemodialysis Access Through the Cephalic Vein, Journal of the American College of Surgeons, 1994, vol. 179, pp. 171-172.
Gravenstein, et al., In Vitro Evaluation of Relative Perforating Potential of Central Venous Catheters: Comparison of Materials, Selected Models, Number of Lumens, and Angles of Incidence to Simulated Membrane, Journal of Clinical Monitoring, 1991, vol. 7, pp. 1-6.
Haindl, H., Technical complications for port-catheter systems, Reg. Cancer Treat, 1989, 2:238-242.
Haire, et at., Thrombotic Complications of Subclavian Apheresis catheters in Cancer Patients: Prevention With Heparin Infusion, Journal of Clinical Apheresis, 1990, vol. 5, pp. 188-191.
Hull, et al., The Groshong Catheter: Initial Experience and Early Results of Imaging-guided Placement1, Radiology, 1992, vol. 185, pp. 803-807.
Ignotus, et al., Review of Radiological Insertion of Indwelling Central Venous Catheters, minimally invasive Therapy, 1992, 1:373-388.
Instructions for Use (Copyright Dated 1990) for Polycath Polyurethance Central Venous Catheter; believed to have been packaged with product believed to have been sold in the United States before Jan. 2000 and related marketing materials.
Instructions for Use (Copyright Dated 1992) for FloLock Single Lumen Bi-directional Valved Catheter; believed to have been packaged with product believed to have been sold in the United States before Jan. 2000.
Instructions for Use (not dated) for Infuse-a-Cath Polyurethance Central Venous Catheter; believed to have been packaged with product believed to have been sold in the United States before Jan. 2000.
Instructions for Use for Diatek Cannon Catheter Product First Sold in the United States Sep. 2001.
Jones, et al., Efficacy of the Supraclavicular Route for Temporary Hemodialysis Access, Southern Medical Journal, 1992, vol. 85, No. 7, pp. 725-726.
Kaupke, et al., Perforation of the Superior Vena Cava by a Subclavin Hemodialysis Catheter: early detection by angiography, The International Journal of Artificial Organs, 1992, vol. 15, No. 11, pp. 666-668.
Kelber, et al., Factors Affecting Delivery of High-Efficiency Dialysis Using Temporary Vascular Access, American Journal of Kidney Diseases, 1993, vol. 22, No. 1, pp. 24-29.
Lumsden, et al., Hemodialysis Access in the Pediatric Patient Population, The American Journal of Surgery, 1994, vol. 168, pp. 197-201.
Lund, "Percutaneous Translumber Inferior Vena Cava Cannulation and other Alternative Vascular Access Techniques" in Venous Interventional Radiology with Clinical Perspectives, Savader et al, eds, pp. 251-261 (date unknown).
Lund, et al., Percutaneous Translumber Inferior Vena Cava Cannulation for Hemodialysis, American Journal of Kidney Diseases, 1995, vol. 25, No. 5, pp. 732-737.
Maki, D., Pathogenesis, Prevention, and Management of Infections Due to Intravascular Devices Used for Infusion Therapy, in Infections Associated with Indwelling Medical Devices, Bisno et al, eds, American Society for Microbiology, 1989, pp. 161-177.
Mauro, et al., Radiologic Placement of Long-term Central Venous Catheters: A Review, JVIR, 1993, vol. 4, No. 1, pp. 127-137.
McGee, et al., Accurate placement of central venous catheters: A prospective, randomized, multicenter trial, Critical Care Medicine, 1993, vol. 21, No. 8, pp. 1118-1123.
Medcomp, "For Access via the Internal Jugular Vein . . . The Medcomp TESIO Catheter is the Solution: The Short and Long Term Solution to Subclavian Venin Stenosis and Difficult Access Problems"—Brochure, 4 pp.
Northsea, C., Using Urokinase to Restore Patency in Double Lumen Catheters, ANNA Journal 1994, vol. 21, No. 5, pp. 261-273.
Parsa, et al., Establishment of Intravenous Lines for Long-term Intravenous Therapy and Monitoring, Surgical Clinics of N. Am. 1985, vol. 65, No. 4, pp. 835-865.

Parsa, et al., Vascular Access Techniques, Monitoring, pp. 122-145 (date unknown).

Pasquale, et al., Groshong® versus Hickman® Catheters, Surgery, Gynecology & Obstetrics, 1992, vol. 174, pp. 408-410.

Passaro, et al., Long-term Silastic Catheters and Chest Pain, Journal of Parenteral andEnteral Nutrition, 1994, vol. 18, Bo. 3, pp. 240-242.

Paulsen, et al., Use of Tissue Plasminogen Activator for Reopening of Clotted Dialysis Catheters, Nephron, 1993, vol. 64, pp. 468-470.

Picture of device believed to be partial sample of a product believed to have been sold in the United States with the Polycath and/or Infuse-a-Cath Instructions for Use, 1 page.

Quinton® Catheter Products (1993).

Raaf, et al., Open Insertion of Right Atrial Catheters Through the Jugular Veins, surgery, Gynecology & Obstetrics, 1993, vol. 177, pp. 295-298.

Schwab, et al., Prospective Evaluation of a Dacron Cuffed Hemodialysis Catheter for Prolonged Use, American Journal of Kidney Diseases, 1998, vol. XI, No. 2, pp. 166-169.

Schwab, et al., Vascular Access: Case Oriented Discussions of Selected Critical Issues: Hemodialysis Catheters for Permanent Use (date unknown).

Shaffer D., lessons from Vascular Access Procedures for Hemodialysis, Surgical Oncology Clinics of North America, 1995, vol. 4, No. 3, pp. 537-549.

Shaffer, D., Catheter-Related Sepsis Complication Long-Term Tunnelled Central Venous Dialysis Catheters: Management by Guidewire Exchange, American Journal of Kidney Disease, 1995, vol. 25, No. 4. pp. 593-596.

Sioshansi, P., New Processes for Surface Treatment of Catheters, Artificial Organs, 1994, 18(4):266-271.

Swartz, et al., Successful Use of Cuffed Central venous Hemodialysis Catheters Inserted Percutaneously, J. Am. Soc. Nephrol., 1994, 4:1719-1725.

Tesio, et al., Double Catherization of the Internal Jugular Vein for Hemodialysis: Indications, Techniques, and Clinical Results, Artificial Organs, 1994, vol. 18, No. 4, pp. 301-304.

Treiman, et al., Chronic Venous Access in Patients with Cancer, Cancer, 1993, vol. 72, No. 3, pp. 760-765.

Twadorski, et al., "Blood Recirculation in Intravenous Catheters for Hemodialysis" J. am. Soc. Nephrol. 3:1978-81 (1993).

Uldall, P. Subclavian Cannulation Is No longer Necessary or justified in Patients with End-Stage Renal failure, Seminar in Dialysis, 1994, vol. 7, No. 3, pp. 161-164.

Wechsler, et al., Thrombosis and Infection Caused by Thoracic Venous Catheters: Pathogenesis and Imagings Findings, AJR, 1993; 160:467-471.

Weitzel, et al., Successful use if Indwelling Cuffed Femoral Vein Catheters in Ambulatory Hemodialysis Patients, America Journal of Kidney diseases, 1993, vol. 22, No. 3, pp. 426-429.

PCT/US2008/082106 filed Oct. 31, 2008 Written Opinion dated Jan. 12, 2009.

Raaf Dual Lumen Right Atrial Catheters Brochure—Quinton Instrument Co., 6 pages, 1993.

Rawn, et al., The Hemodialysis Access, Chapter 9, pp. 9.1-9.11.

Tal, Michael G. Comparison of Recirculation Percentage of the Palindrome Catheter and Standard Hemodialysis Catheters in a Swine Model, J Vasc Interv Radiol, pp. 1237-1240, vol. 16, No. 9, 2005.

The Groshong™ Peripherally Inserted Central Venous Catheter Brochure—Cath-tech®, 4 pages, 1988.

Transcript of Videotaped Deposition of Gregory Haas (Excerpt), Sep. 23, 2003, *Thierry Pourchez and Bard Access Systems, Inc.* v. *Diatek, Inc. and Arrow International, Inc.*, Civil Action No. 03-CV-0972 (S.D.N.Y).

Transcript of Videotaped Deposition of Thierry Pourchez, vol. 1, Oct. 16, 2003, *Thierry Pourchez and Bard Access Systems, Inc.* v. *Diatek, Inc. and Arrow International, Inc.*, Civil Action No. 03-CV-0972 (S.D.N.Y).

Transcript of Videotaped Deposition of Thierry Pourchez, vol. 2, Oct. 17, 2003, *Thierry Pourchez and Bard Access Systems, Inc.* v. *Diatek, Inc. and Arrow International, Inc.*, Civil Action No. 03-CV-0972 (S.D.n.Y).

Twardowski et al. "Side Holes at the Tip of Chronic Hemodialysis Catehters are Harmful," The Journal of Vascular Access 2001; 2:8-16.

Twardowski, et al., Side Holes at the Tip of Chronic Hemodialysis Catheters are Harmful, The Journal of Vascular Access 2001; 2: 8 16.

TYCO Healthcare, MAHURKAR Dual Lumen Catheters, Informational Brochure, 2 pages, 2004.

TYCO Healthcare, MAHURKAR QPlus High Flow Acute Care Catheter, Informational Brochure, 2 pages, 2004.

TYCO Healthcare, Tal PALINDROME™ Dual Lumen Catheters Order Information, Features and Benefits, Frequently Asked Questions, printed from http://www.kendallvasculartherapy.com/VascularTherapy, 6 pages, on Mar. 1, 2007.

U.S. Appl. No. 10/445,731, filed May 27, 2003 Non-Final Office Action dated Apr. 13, 2007.

U.S. Appl. No. 10/445,731, filed May 27, 2003 Non-Final Office Action dated Dec. 12, 2008.

U.S. Appl. No. 10/445,731, filed May 27, 2003 Non-Final Office Action dated May 30, 2008.

U.S. Appl. No. 10/874,298, filed Jun. 9, 2004 Advisory Action dated Feb. 19, 2009.

U.S. Appl. No. 10/874,298, filed Jun. 9, 2004 Final Office Action dated Jul. 15, 2008.

U.S. Appl. No. 10/874,298, filed Jun. 9, 2004 Final Office Action dated Jul. 7, 2010.

U.S. Appl. No. 10/874,298, filed Jun. 9, 2004 Non-Final Office Action dated Aug. 18, 2011.

U.S. Appl. No. 10/874,298, filed Jun. 9, 2004 Non-Final Office Action dated Dec. 30, 2009.

U.S. Appl. No. 10/874,298, filed Jun. 9, 2004 Non-Final Office Action dated Feb. 2, 2011.

U.S. Appl. No. 10/874,298, filed Jun. 9, 2004 Non-Final Office Action dated Jul. 23, 2009.

U.S. Appl. No. 10/874,298, filed Jun. 9, 2004 Non-Final Office Action dated May 23, 2006.

U.S. Appl. No. 10/874,298, filed Jun. 9, 2004 Non-Final Office Action dated May 24, 2007.

U.S. Appl. No. 11/859,106, filed Sep. 21, 2007 Final Office Action dated Sep. 1, 2009.

U.S. Appl. No. 11/859,106, filed Sep. 21, 2007 Non-Final Office Action dated Mar. 30, 2011.

U.S. Appl. No. 11/859,106, filed Sep. 21, 2007 Non-Final Office Action dated Jun. 25, 2008.

U.S. Appl. No. 12/048,871, filed Mar. 14, 2008 Final Office Action dated Jan. 20, 2011.

U.S. Appl. No. 12/048,871, filed Mar. 14, 2008 Non-Final Office Action dated Jan. 7, 2010.

U.S. Appl. No. 12/048,871, filed Mar. 14, 2008 Non-Final Office Action dated Jul. 7, 2010.

U.S. Appl. No. 12/048,871, filed Mar. 14, 2008 Non-Final Office Action dated May 12, 2009.

U.S. Appl. No. 12/244,544, filed Oct. 2, 2008 Final Office Action dated Jul. 11, 2011.

U.S. Appl. No. 12/244,544, filed Oct. 2, 2008 Non-Final Office Action dated Dec. 22, 2010.

U.S. Appl. No. 12/244,554, filed Oct. 2, 2008 Final Office Action dated Dec. 27, 2010.

U.S. Appl. No. 12/244,554, filed Oct. 2, 2008 Non-Final Office Action dated Jul. 6, 2010.

U.S. Appl. No. 12/253,870, filed Oct. 17, 2008 Non-Final Office Action dated Jan. 21, 2011.

U.S. Appl. No. 12/253,870, filed Oct. 17, 2008 Notice of Allowance dated Aug. 19, 2011.

U.S. Appl. No. 12/262,820, filed Oct. 31, 2008 Non-Final Office Action dated Feb. 18, 2011.

U.S. Appl. No. 12/263,141, filed Oct. 31, 2008 Advisory Action dated Aug. 17, 2011.

U.S. Appl. No. 12/263,141, filed Oct. 31, 2008 Final Office Action dated May 26, 2011.

U.S. Appl. No. 12/263,141, filed Oct. 31, 2008 Non-Final Office Action dated Jan. 5, 2011.

U.S. Appl. No. 12/414,467, filed Mar. 30, 2009 Non-Final Office Action dated Aug. 11, 2011.

U.S. Appl. No. 10/842,586, filed May 10, 2004 Advisory Action dated Oct. 9, 2008.

U.S. Appl. No. 10/842,586, filed May 10, 2004 Final Office Action dated May 25, 2010.
U.S. Appl. No. 10/842,586, filed May 10, 2004 Final Office Action dated Jul. 29, 2008.
U.S. Appl. No. 10/842,586, filed May 10, 2004 Non-Final Office Action dated Jan. 7, 2008.
U.S. Appl. No. 10/842,586, filed May 10, 2004 Non-Final Office Action dated Jun. 16, 2009.
U.S. Appl. No. 10/842,586, filed May 10, 2004 Non-Final Office Action dated Nov. 13, 2008.
U.S. Appl. No. 10/842,586, filed May 10, 2004 Non-Final Office Action dated Nov. 23, 2009.
*Arrow International, Inc. et al v. Spire Biomedical, Inc.*, U.S. Dist Ct Dist MA CA No. 06-CV-11564-DPW, Declaration of Dr. Karim Valji (Jul. 17, 2008).
*Arrow International, Inc. et al v. Spire Biomedical, Inc.*, U.S. Dist Ct Dist MA CA No. 06-CV-11564-DPW, Declaration of Kenneth Todd Cassidy (Jul. 16, 2008).
*Arrow International, Inc. et al v. Spire Biomedical, Inc.*, U.S. Dist Ct Dist MA CA No. 06-CV-11564-DPW, Declaration of Rebecca R. Eisenberg in Opposition to Defendant's Motion for Partial Summary Judgment of Invalidity (Jun. 8, 2009).
*Arrow International, Inc. et al v. Spire Biomedical, Inc.*, U.S. Dist Ct Dist MA CA No. 06-CV-11564-DPW, Memorandum of Law in Support of Defendant's Motion for Summary Judgment on Invalidity [Redacted Pursuant to Jun. 10, 2008 Order on Motion to Seal].
*Arrow International, Inc. et al v. Spire Biomedical, Inc.*, U.S. Dist Ct Dist MA CA No. 06-CV-11564-DPW, Memorandum of Law in Support of Defendant's Motion for Summary Judgment on Invalidity Exhibit A (Jul. 10, 2009).
*Arrow International, Inc. et al v. Spire Biomedical, Inc.*, U.S. Dist Ct Dist MA CA No. 06-CV-11564-DPW, Plaintiff's Memorandum in Opposition to Defendant's Motion for Summary Judgement on Non-Infringement (Jul. 17, 2008).
*Arrow International, Inc. et al. v. Spire Biomedical, Inc.*, U.S. Dist. Ct. Dist. MA CA No. 06-CV-11564-DPW, Defendant's Omnibus Statement of Material Facts in Support of its Motions for Summary Judgment [Redacted Pursuant to Jun. 10, 2007 Order on Motion to Seal].
BARD Access Systems Hickman®, Leonard®, and Broviac® Central Venous Catheters (Long Term), Instructions for Use, 31 pages, 1999.
BARD Access Systems Hickman®, Leonard®, and Broviac® Central Venous Catheters, Nursing Procedural Manual, 52 pages, Jun. 1994.
BARD Davol® Hickman® Round Dual Lumen Catheters for Central Venous Access Informational Brochure, 2 pages, 1994.
BARD Hickman® Catheters Informational Brochure, 3 pages, 1994.
CAMP, "Care of the Groshong Catheter", Oncol Nurs Forum, vol. 15, No. 6, 1988.
Declaration of Gregory S. Haas (Plaintiff's Exhibit 88 in Haas Deposition), Mar. 13, 2003, *Thierry Pourchez and Bard Access Systems, Inc. v. Diatek, Inc. and Arrow International, Inc.*, Civil Action No. 03-CV-0972 (S.D.N.Y.).
Defendant's Exhibits DX78-DX114, *Thierry Pourchez and Bard Access Systems, Inc. v. Diatek, Inc. and Arrow International, Inc.*, Civil Action No. 03-CV-0972 (S.D.N.Y.).
Defendants' Reponses and Objections to Plaintiffs' Second Set of Interrogatories (Excerpt), *Thierry Pourchez and Bard Access Systems, Inc. v. Diatek, Inc. and Arrow International, Inc.*, Civil Action No. 03-CV-0972 (S.D.N.Y.) (Oct. 8, 2003).
Delmore et al., "Experience with the Groshong Long-Term Central Venous Catheter", Gynecologic Oncology 34, 216-218 (1989).
Dialysis Vascular Access, SchonXL® Temporary Dialysis (AngioDynamics Inc.) brochure.
Difiore, "Central Venous Dialysis Catheter Evaluatio in Swine", Journal of Vascular Access Devices, Fall 2000.
Dupont et al, Long-term development of Permacath Quinton catheters used as a vascular access route for extra-renal detoxification; Néphrologie, vol. 15, pp. 105-110, 1994.
EP 04712925.9 filed Feb. 19, 2004 Office Action dated Nov. 7, 2008.
EP 08839196.6 filed Oct. 2, 2008 Search Opinion dated Jul. 12, 2011.
EP 08839196.6 filed Oct. 2, 2008 Search Report dated Jul. 12, 2011.

JP App. No. 2003-565569 filed Feb. 7, 2003, Translated Decision of Refusal mailed Dec. 24, 2009.
JP App. No. 2003-565569 filed Feb. 7, 2003, Translated Official Action mailed May 28, 2009.
JP App. No. 2003-565569 filed Feb. 7, 2003, Translated Official Action mailed Nov. 7, 2008.
Kapoian et al. Dialysis as Treatment of End-Stage Renal Disease, Chapter 5: Dialysis Access and Recirculation.
Malviya et al., "Vascular Access in Gynecological Cancer Using the Groshong Right Atrial Catheter", Gynecological Oncology 33, 313-316 (1989).
Medcomp® Brochure, "Ash Split Cath™ XL", Dec. 2001, PN 2291.
Medcomp® Brochure, "Ash Split Cath™", Guidewire Weave Insertion Technique, Jan. 2002, PN 2296.
Medcomp® Brochure, "Ash Split Cath™", Jul. 2001, PN 2114.
Medcomp® Brochure, "Ash Split Cath™", Nov. 1997, PN 2050.
Medcomp® Brochure, "Ash Split Cath® II", Aug. 2002, PN 2334.
Medcomp® Brochure, "Magna™ High Flow Catheter", Mar. 2002, PN 2321.
Moss, et al., Use of a Silicone Catheter With a Dacron Cuff for Dialysis Short-Term Vascular Access, American Journal of Kidney Diseases, 1988, vol. XII, No. 6, pp. 492-498.
Myers, R.D. et al, New Double-lumen Polyethylene Cannula for Push-pull Perfusion of Brain Tissue in Vivo, Journal of Neuroscience Methods, pp. 205-218, vol. 12, 1985.
Patel et al., "Sheathless Technique of Ash Split-Cath Insertion", 12 JVIR 376-78 (Mar. 2001).
PCT/US2003/003751 filed Feb. 7, 2003 Preliminary Examination Report dated May 5, 2004.
PCT/US2003/003751 filed Feb. 7, 2003 Search Report dated Jul. 3, 2003.
PCT/US2004/005102 filed Feb. 19, 2004 Preliminary Report Patenability dated Aug. 29, 2005.
PCT/US2004/005102 filed Feb. 19, 2004 Search Report dated Dec. 27, 2004.
PCT/US2008/078551 filed Oct. 2, 2008 International Preliminary Report on Patentability dated Apr. 20, 2010.
PCT/US2008/078560 filed Oct. 2, 2008 Preliminary Report on Patentability dated Aug. 26, 2010.
PCT/US2008/078566 filed Oct. 2, 2008 International Preliminary Report on Patentability dated Apr. 20, 2010.
PCT/US2008/078571 filed Oct. 2, 2008 Preliminary Report on Patentability dated Aug. 26, 2010.
PCT/US2008/080463 filed Oct. 20, 2008 Preliminary Report on Patentability dated Apr. 27, 2010.
PCT/US2008/080463 filed Oct. 20, 2008 Search Report dated Mar. 16, 2009.
PCT/US2008/080463 filed Oct. 20, 2008 Written Opinion dated Apr. 16, 2009.
PCT/US2008/082106 filed Oct. 31, 2008 International Preliminary Report on Patentability dated May 4, 2010.
PCT/US2008/082106 filed Oct. 31, 2008 Search Report dated Jan. 12, 2009.
CN 200880121182.0 filed Oct. 20, 2008 First Office Action dated May 2, 2012.
CN 200880121183.5 filed Oct. 2, 2008 First Office Action dated Mar. 28, 2012.
CN 200880121183.5 filed Oct. 2, 2008 Second Office Action dated Aug. 17, 2012.
CN 200880121183.5 filed Oct. 2, 2008 Third Office Action dated Dec. 11, 2012.
CN 200880123095.9 filed Oct. 20, 2008 First Office Action dated Feb. 13, 2012.
CN 200880123095.9 filed Oct. 20, 2008 Second Office Action dated Dec. 18, 2012.
CN 200880123533.1 filed Jun. 30, 2008 First Office Action dated May 28, 2012.
CN 200880123533.1 filed Jun. 30, 2008 Notice of Grant dated Dec. 24, 2012.
EP 08839196.6 filed Oct. 2, 2008 Examination Report dated Jan. 16, 2013.
EP 08872340.8 filed Oct. 2, 2008 Extended European Search Report and an Opinion dated Apr. 19, 2012.

JP 2010-532299 filed Apr. 30, 2010 Final Notice of Reason for Rejection dated Feb. 8, 2013.

JP 2010-532299 filed Apr. 30, 2010 Official Action dated Apr. 23, 2012. X.

Septum, Wikipedia, The Free Encyclopedia, hhtp://en.wikipedia.org/wiki/Septum (last visited Dec. 18, 2012) (defining "septum" as "A wall, dividing a cavity or structure into smaller ones").

Taber's Cyclopedic Medical Dictionary 1662 (16th ed. 1989) (defining "septum" as a "wall dividing two cavities").

U.S. Appl. No. 10/371,774, filed Feb. 21, 2003 Final Office Action dated Jan. 19, 2007.

U.S. Appl. No. 10/371,774, filed Feb. 21, 2003 Final Office Action dated Mar. 7, 2007.

U.S. Appl. No. 10/371,774, filed Feb. 21, 2003 Non-Final Office Action dated Jul. 17, 2006.

U.S. Appl. No. 10/371,774, filed Feb. 21, 2003 Notice of Allowance dated Jun. 1, 2007.

U.S. Appl. No. 11/859,106, filed Aug. 21, 2007 Non-Final Office Action dated Feb. 5, 2009.

U.S. Appl. No. 11/874,447, filed Oct. 18, 2007 Decision on Appeal dated Dec. 26, 2012.

U.S. Appl. No. 11/874,447, filed Oct. 18, 2007 Examiner's Answer dated Apr. 28, 2010.

U.S. Appl. No. 11/874,447, filed Oct. 18, 2007 Final Office Action dated Jul. 22, 2009.

U.S. Appl. No. 11/874,447, filed Oct. 18, 2007 Non-Final Office Action dated Jan. 6, 2009.

U.S. Appl. No. 11/874,447, filed Oct. 18, 2007 Non-Final Office Action dated Jul. 9, 2008.

U.S. Appl. No. 12/048,871, filed Mar. 14, 2008 Examiner's Answer dated Feb. 9, 2012.

U.S. Appl. No. 12/244,559, filed Oct. 2, 2009 Final Office Action dated Jul. 3, 2012.

U.S. Appl. No. 12/244,559, filed Oct. 2, 2009 Non-Final Office Action dated Mar. 14, 2012.

U.S. Appl. No. 12/262,820, filed Oct. 31, 2008 Notice of Allowance dated Sep. 28, 2011.

U.S. Appl. No. 12/414,467, filed Mar. 30, 2009 Final Office Action dated Feb. 7, 2012.

U.S. Appl. No. 12/414,467, filed Mar. 30, 2009 Notice of Allowance dated May 31, 2012.

U.S. Appl. No. 13/445,713, filed Apr. 12, 2012 Non-Final Office Action dated Jan. 2, 2013.

US Patent File History USPN 5,403,291 (Abrahamson).

US Patent File History USPN 5,489,278 (Abrahamson).

US Patent File History USPN 5,685,867 (Twardowski et al.).

* cited by examiner

MANUFACTURE OF SPLIT TIP CATHETERS

CROSS REFERENCE TO RELATED APPLICATIONS

This application claims the benefit of priority to U.S. Provisional Application No. 60/980,633, filed Oct. 17, 2007, and titled "Manufacture of Split Tip Catheters," which is incorporated by reference in its entirety herein. The following three applications, filed concurrently herewith, are related to the subject matter of this application and are incorporated by reference in their entirety herein: 1) U.S. patent application Ser. No. 12/244,554, titled "Catheters With Enlarged Arterial Lumens," and published as US 2009/0204079; 2) U.S. patent application Ser. No. 12/244,544, titled "Fusion Manufacture of Multi-Lumen Catheters," and published as US 2009/0209940; and 3) U.S. patent application Ser. No. 12/244,559, titled "Manufacture of Fixed Tip Catheters," and published as US 2009/0205189.

BACKGROUND

The present invention generally relates to catheters and preferably to multi-lumen catheters used for vascular access.

Multi-lumen catheters and, in particular split-tip catheters, are desirable for various treatment applications such as hemodialysis where fluid extraction and return occur simultaneously. Hemodialysis is the separation of metabolic waste products and water from the blood by filtration. Typically, a hemodialysis unit is connected to a patient's body by a catheter. The catheter's distal end is placed in a blood vessel and its proximal end is connected to a hemodialysis unit.

During hemodialysis, a patient's blood typically flows through a double lumen catheter to the hemodialysis unit which provides filtration and controls the flow of blood. A double lumen catheter has two lumens that independently allow fluid extraction and return. For example, one lumen can be used for removing blood from a patient for processing in the hemodialysis machine and the other lumen can be used for subsequently returning the processed blood back to the patient's circulatory system. Such catheters can also include additional lumens for flushing, administration of anticoagulants or the like.

Parameters that can be varied to achieve adequate hemodialysis include blood flow rate, dialysis solution flow rate, and dialyzer competency. Generally, raising the blood flow rate increases dialysis efficiency. However, conditions such as access recirculation decrease efficiency. Access recirculation is the recirculation of treated blood back into the hemodialysis unit. Excess recirculation effectively reduces dialysis efficiency and lengthens the duration of the treatment needed for adequate dialysis. Access recirculation can be particularly of concern when using a double lumen catheter due to the close proximity of the intake and outflow ports at the distal tip of the catheter.

Various double lumen catheter designs have been suggested for the purpose of reducing access recirculation. The distal ends of intake and outflow lumens have been longitudinally spaced 20-30 mm apart to prevent recirculation. For example, Twardowski et al. U.S. Pat. No. 5,569,182 discloses that the lumen for return of blood back into the vein should terminate beyond the extraction lumen. The purpose of this is to prevent cleansed blood, exiting from the outlet point of the catheter, from re-entering the catheter's blood inlet point and returning to the dialysis machine. However, certain disadvantages have been noted by such large longitudinal spacing between the distal ends of the respective lumens. For example, blood flow stagnation in the region of the blood vessel between two widely separated tips can lead to clot formation.

In addition to longitudinal spacing of the distal openings of the lumens, others have suggested that the distal end of a multi-lumen catheter can be split such that the distal tip segments can independently move in the blood vessel to optimize the fluid dynamics of the different functions (blood extraction and blood return). The introduction of an angle between the extraction and return lumens of a split tip catheter can further reduce the likelihood of access recirculation due to greater separation between inflow and outflow lumens.

Moreover, it can be desirable to have the maximum possible luminal cross-sectional areas to optimize catheter flow characteristics and also to maintain adequate flow over time since flow rates tend to decrease due to factors such as catheter clotting. However, a need can remain to maintain adequate physical and mechanical properties of the catheter, for instance tensile strength and kink-resistance, and to keep overall catheter dimensions small enough for insertion and proper physiological function. With these constraints in mind, it can be advantageous to have a different shape, e.g., greater luminal cross-section, for one or the other of the lumens or split tip segments, for example, to facilitate blood withdrawal or to diffuse returning cleansed blood. In particular, the arterial (or extraction) lumen is more prone to clogging and can benefit from having a larger cross-section. However, such geometric differences are difficult to incorporate into split-tip catheters using conventional manufacturing techniques.

While various techniques are known for manufacturing split tip catheters, there exists a need for more efficient and more robust techniques, especially in manufacturing split tip catheters when the divergence of the tip elements at an angle is desired or a different shape or geometry is desired for one or the other of the lumens or tip segments.

SUMMARY OF THE INVENTION

Multi-lumen catheter devices having at least one split end are disclosed, together with methods of forming such split tip catheters. In one aspect of the invention, the manufacturing methods can include the steps of: providing a catheter body having at least a first and a second internal lumen extending longitudinally through the catheter body; removing a distal portion of the catheter body to form a first distal tip segment such that the first lumen extends longitudinally within this tip segment beyond the second lumen; and joining a second lumen tip segment to the catheter body in communication with the second lumen. The second tip segment can be joined to the catheter body such that it is at least partially separated from the first tip segment and, in some embodiments, preferably diverges at an angle relative to the first tip segment.

The second lumen tip segment can be joined to the device by various techniques. For example, the second segment can be joined to the catheter body by thermal or chemical fusion. Alternatively, the second lumen tip segment can be bonded to the catheter body with an adhesive or the like.

In one embodiment of the invention, the second lumen tip segment can be oriented such that the first and second tip segments are separate and diverge from each other at an angle. The angle between the first and second tip segments can be formed before, during, or after the second tip segment is joined to the catheter body. For example, the angle can be formed after joining the segment to the catheter body by the application of heat. Alternatively, the catheter body and/or the second segment can present an angled interface such that an angle is formed at the joint itself. The angle between the first and second tip segments can change from a proximal end of the first and second tip segments to a distal end of the first and second tip segments, e.g., one or both of the separate tip segments can be a compound angle or formed in the shape of a simple or compound curve.

In another embodiment of the invention, the second lumen tip segment can be oriented such that the first and second tip segments are separate but substantially parallel to each other.

Split tip catheters according to the invention can be formed by removing a distal portion of the catheter body by slicing away one of the lumens. If an angled separation is desired, the method can further include trimming the lumen in a non-perpendicular direction with respect to a longitudinal axis of the catheter body to facilitate attachment of the second tip segment at an angle. Alternatively, if substantially parallel split tips are desired, the method can further include trimming the lumen in a direction that is substantially perpendicular to a longitudinal axis of the trimmed lumen.

The catheters of the present invention can further include forming fluid passage holes in a side of at least one of the tip segments. In another aspect, the catheters of the present invention can further include coatings of at least a portion of the catheter body or the first and/or second tip segments with an antithrombotic agent, such as heparin, to reduce blood clotting or protein adhesion. In other aspects, the catheters of the present invention can include coatings of at least a portion of the body or the first and/or second tip segments with an antibacterial agent and/or an anti-inflammatory agent.

Additionally, following (or during) formation of the split tip catheter, the first and second tip segments can be joined together with a bioresorbable adhesive to simplify vascular insertion. Following insertion, the tip segments can separate upon dissolution of the adhesive, e.g., over a period of time ranging from 1 second to several days, more preferably from about 1 minute to about 10 hours, or 5 hours or one hour.

In another aspect of the invention, a method of forming a split tip catheter is disclosed including the steps of: (a) providing a multi-lumen catheter having at least a first inner lumen and a second inner lumen extending therethrough; (b) partially truncating a distal end of the multi-lumen catheter body to form a first distal lumen tube such that the first lumen of the catheter within the first distal tube longitudinally extends further than at least a second lumen of the catheter; and (c) attaching a second lumen tube to the severed end of the catheter such that a second distal lumen tube in fluid communication with the second lumen of the catheter is formed and extends longitudinally from the catheter separate from the first distal lumen tube.

The method can further include forming a non-zero angle between the first distal tube and the second distal tube. A non-zero-angle can be formed, for example, by trimming the catheter body at an angle, e.g., in a non-perpendicular direction with respect to a longitudinal axis of the first distal lumen tube, and then fusing or bonding the second distal tube to the catheter body at this location. The term "fusing" is used interchangeably with "bonding" herein and, as used, both terms are intended to encompass thermal fusion, melt bonding, ultrasonic welding, chemical bonding, adhesive bonding and the like.

Alternatively, the first and second distal end tubes can be formed with substantially a zero angle of divergence, e.g., the two end segments are substantially parallel to each other in a rest position. A zero-angle can be formed, for example, by trimming the catheter body in a perpendicular direction with respect to a longitudinal axis of the first distal lumen tube, and then fusing or bonding the second distal tube to the catheter body at this location.

In certain embodiments, it may be preferable that the second distal tube (that is to be joined to the catheter body) have a different luminal cross-section than the second lumen within the catheter body or that the first and second lumens within the catheter body have a different luminal cross-section from one another. The invention is also applicable to catheters having three or more lumens. For example, a three lumen catheter body can be truncated such that only one distal lumen extends from the point of truncation and then two separate end tubes can be grafted onto the body to provide three independent distal tip segments. Alternatively, the two grafted segments can be attached together but joined to the body separately from the first segment (formed from the original catheter body). In another alternative, the three lumen catheter body can be truncated such that two of the lumens extend in a distal segment from the point of truncation with a separate end tube grafted onto the body to provide a separated third lumen.

The present invention is advantageous, among other reasons, because only one distal tip segment is bonded to the catheter body (in contrast to prior art where two tip segments must be bonded), thus simplifying the process and shortening the manufacturing time. A further advantage is that bonding a single distal tip segment permits reduced septum thickness in the catheter body (and therefore increased luminal cross-sections) since the septum does not have to accommodate the attachment of two separate distal end tubes.

The method is particularly useful when one or more of the lumens has a non-circular cross-section, e.g., a substantially D-shaped cross-section. For example, the catheter body can be formed in a "double-D" configuration, with two "D" shaped lumens back-to-back and separated by a septum. A catheter body with a septum between the lumens can be formed by various means, e.g., as an integral body by extrusion or by assembling two D-shaped single lumen elements and then surrounding them by a sheath of heat-shrink polymeric material, thereby forming an integral body.

The method according to the invention can further include the step of partially truncating the catheter body further comprises truncating the body at a truncation point such that at least a portion of the septum (and preferably a major portion or all of the septum) is retained by the first distal lumen tube. Moreover, the method can further include attaching the second distal tube at least partially to the septum of the first distal tube.

The method according to the invention can further include the step of attaching a second distal tube that has a different shape than the first or second lumens of the catheter body. (The term "shape" is used herein to encompass differences in geometry, e.g., circular, ellipsoid or D-shaped as well as differences in size, e.g., cross-sectional area of the lumens.)

In another aspect of the invention, a method of forming a split tip catheter is disclosed, wherein the method can include the steps of: (a) truncating the catheter body at a septum dividing two of the lumens such that a first distal end tube is formed and the first tube surrounds a first lumen having a length that extends beyond a truncation point; and (b) attaching a second distal end lumen tube to the catheter body in fluid communication with a second lumen of the catheter body.

In yet another aspect of the invention, another method of forming a split tip catheter is disclosed including the steps of: (a) removing a partial length of a lumen included in a catheter body to expose a septum between the lumen and another lumen included in the catheter body, wherein each lumen defines a separate fluid pathway extending longitudinally through the body; and (b) attaching a replacement lumen tube at a distal end of the catheter body such that a pathway extending longitudinally through the replacement lumen tube is in communication with the pathway of the lumen that was partially removed. Again, the two (or more) lumen tubes can be formed to either diverge at an angle or to remain parallel to each other. (The term "parallel," as used herein, is intended to encompass configurations that nominally have a "zero" angle of divergence as well as slight angles that may exist due to practical constraints or machining tolerances. It should also be appreciated that the preferred materials for the catheters of this invention are polymeric materials, such as polyurethane or silicone, that will also exhibit flexibility or "floppiness," in both their parallel and divergence configurations.)

The step of removing the partial length of the lumen can further include trimming the lumen opening at a zero or non-zero angle in relation to an axis perpendicular to a longitudinal axis of the catheter. The end of the replacement lumen tube to be joined to the catheter body can also be cut at an angle.

In another aspect of the invention, a method of forming a split tip catheter is disclosed including the steps of: (a) providing a multi-lumen catheter body having at least a first inner lumen and a second inner lumen extending therethrough; (b) partially truncating the multi-lumen catheter body such that a first distal lumen tube is formed to longitudinally extend the first lumen of the catheter further than at least the second lumen of the catheter; and (c) attaching a second lumen tube to the truncated end of the catheter such that a pathway separate from the first distal tube is formed in fluid communication with the second lumen of the catheter, wherein the first inner lumen has a different shape than the second inner lumen.

In a further aspect of the invention, split tip catheter devices are disclosed. In one embodiment the split tip catheter can include a catheter body; a first lumen included in the catheter body, the first lumen having an inner pathway extending longitudinally through the catheter body; a second lumen included in the catheter body, the second lumen having an inner pathway extending longitudinally through the catheter body and a length less than a length of the first lumen; and a lumen tip segment attached to the second lumen and having a pathway extending longitudinally through the lumen tip segment such that the pathway of the lumen tip segment is in communication with the pathway of the second lumen.

Catheter devices according to the invention can be formed such that at least a part of one of the lumen tip segments is composed of a material different than a material of the catheter body. In certain embodiments, the first lumen and the lumen tip segment are separate and diverge from each other at an angle at a distal end of the catheter body. In other embodiments, the first lumen and the lumen tip segment are separate but substantially parallel to each other.

In yet another embodiment, a split tip catheter device is disclosed including a catheter body; a first distal tip segment integral with the catheter body, the first distal segment having an inner pathway extending longitudinally through a first lumen of the catheter body; and a second distal tip segment separate from the first distal segment and joined to the catheter body to provide a fluid pathway from a second lumen of the catheter body and extending longitudinally through the second tip segment.

Other advantages and features will become apparent from the following description and from the claims.

BRIEF DESCRIPTION OF THE DRAWINGS

The invention will be more fully understood from the following detailed description taken in conjunction with the accompanying drawings, in which like reference numerals designate like parts throughout the figures, and wherein.

DETAILED DESCRIPTION

Figure 1:
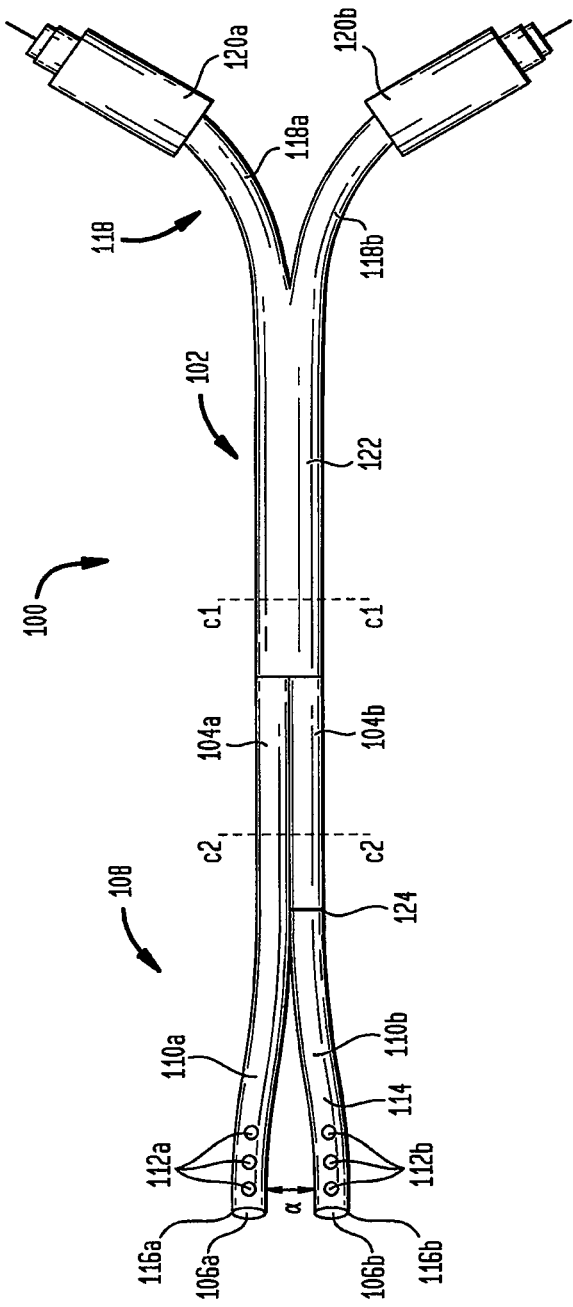
FIG. 1 is a schematic, partially cutaway, side view of a catheter according to the present invention.

In FIG. 1 an embodiment of a split tip catheter 100 according to the invention is shown having a catheter body 102 with two internal lumens 104a, 104b (collectively, the lumens 104). The lumens 104 include respective inner lumen pathways 106a, 106b (collectively, the pathways 106) extending longitudinally through the catheter body 102. The catheter body 102 has a split-tip distal end 108 in which the catheter body 102 (and the lumens 104) separate into two distal lumen tip segments, 110a, 110b (collectively, the lumen tips 110). One of the lumens 104b has been trimmed to a length less than the other lumen 104a. A lumen tip segment 114 has been joined to the trimmed lumen 104b such that the lumen tip 110b includes the lumen tip segment 114 and such that the lumen tip segment 114 is in fluid communication with the trimmed lumen 104b. The lumen tip 110b forms an angle α with respect to the other lumen tip 110a. The value of α can be zero or non-zero and is preferably in the range of zero to ninety degrees. The lumen tips 110 can, but need not, have one or more fluid passage holes 112a, 112b (collectively, the fluid passage holes 112) in fluid communication with their respective lumen 104 to facilitate fluid removal (typically through lumen 104b) and return (typically through lumen 104a), e.g., blood removal and return during hemodialysis. Alternatively, or in conjunction with the fluid passage holes 112, one or both distal ends 116a, 116b (collectively, the distal ends 116) of the lumens 104 can be open to provide fluid passageways through the pathways 106, e.g., for blood removal and return. A proximal end 118 of the catheter body 102 can also be split into separate segments 118a, 118b and terminate with two access ports 120a, 120b, which can include couplings, such as Luer-locks or the like, to couple the catheter 100 to a hemodialysis machine in which blood is circulated and purified. The catheter body 102 is typically a very flexible silicone, polyurethane, or other biocompatible composition (e.g., having a stiffness in the range of about 65 to about 85 durometer), and can include any type of catheter (e.g., a hemodialysis catheter or a central venous catheter).

The catheter body 102 can include an outer sheath 122 which partially or entirely covers and encloses the lumens 104. The outer sheath 122 can be any shape and size and can be made of the same material as the lumens 104 or other material compatible with insertion into a blood vessel. As illustrated in this embodiment, the outer sheath 122 terminates proximal to the distal ends 116 of the lumens 104 such that the lumen tips 110 of each lumen 104 are separate or can separate from one another after being inserted into a blood vessel.

Figure 2:
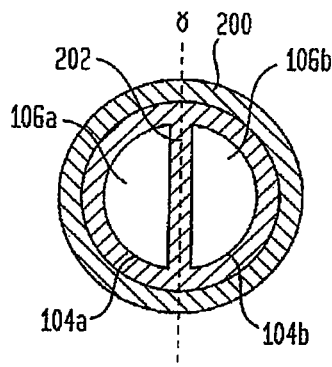
FIG. 2 is a cross-section view of an embodiment of the present invention showing a catheter construction formed from opposed D-shaped lumen bodies inside an outer sheath.

FIG. 2 shows a cross-section c1-c1 of one embodiment of the outer sheath 122. The outer sheath 122 can be of any thickness and can have varying inner and outer shapes as well as varying inner and outer dimensions. The catheter body 102 can be constructed such that sheath material 200 encases the lumens 104a and 104b and no space remains between the sheath and the lumens. For example, the sheath can be fused to the lumens or heat-shrunk around them.

The lumens 104 can have a variety of cross-sectional shapes and sizes but preferably, as shown in the embodiment in FIG. 1, the catheter body 102 has a substantially elliptical (circular or oval) shape and the lumens 104 are each D-shaped. However, one or both of the lumens 104 can transition from one shape to another along at least a portion of its length, e.g., transition from a D-shaped cross-section to a circular cross-section. Furthermore, each of the lumens 104 can have a cross-sectional shape, size, or area that can be the same or distinct from the catheter body 102 and/or the other lumen, as shown in examples of c2-c2 cross-sections in FIGS. 3-10.

Figure 3:
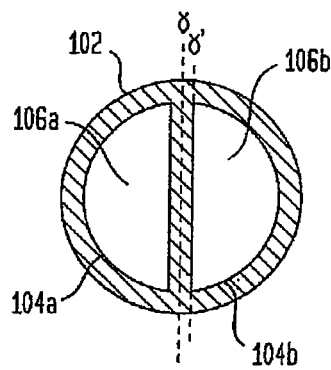
FIG. 3 is a cross-section view of an embodiment of the present invention showing a unibody catheter construction utilizing opposed D-shaped lumens.

FIG. 3 is a cross-section view of an embodiment showing unibody construction utilizing opposed D-shaped lumens 104 having substantially the same size of pathways 106. This configuration eliminates the sheath as a distinct element. The device of FIG. 3 can be formed, for example, by extrusion molding of a catheter body with a plurality of lumens integrated therein. In one embodiment according to the invention the end portion of the catheter body 102 can be truncated by splitting the body along either the center line γ of the longitudinal axis or along an off-center longitudinal axis γ'. In certain applications, truncation along off-center line γ can be preferably because it preserves most or all the septum 202, while sacrificing part of the other lumen 104a (e.g., the part extending distally beyond the cut point 124 as shown in FIG. 1).

Figure 4:
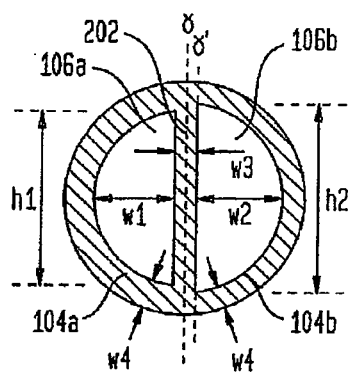
FIG. 4 is a cross-section view of a variation of an embodiment of the present invention showing opposed D-shaped lumens of different cross-sectional areas.
Figure 5:
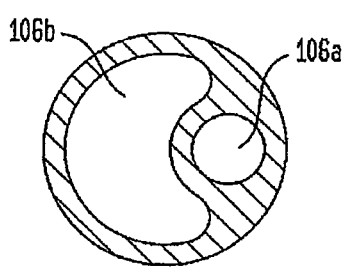
FIG. 5 is a cross-section view of an embodiment of the present invention showing yet another unibody construction with lumens of different shape and size.
Figure 6:
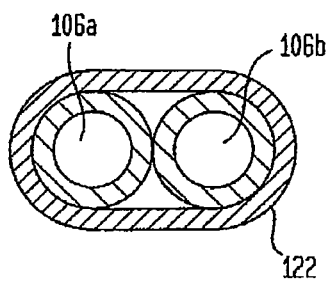
FIG. 6 is a cross-section view of an embodiment of the present invention showing a unibody construction formed from two individual circular lumens inside an outer sheath.
Figure 7:
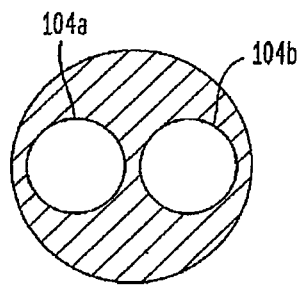
FIG. 7 is a cross-section view of an embodiment of the present invention showing a unibody construction with two individual circular lumens.
Figure 8:
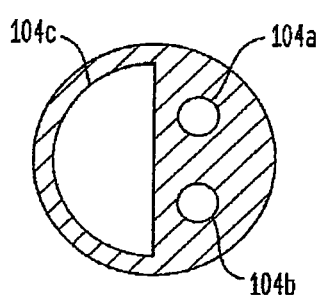
FIG. 8 is a cross-section view of an embodiment of the present invention showing a unibody construction with three lumens.
Figure 9:
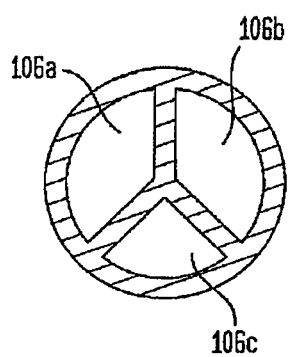
FIG. 9 is a cross-section view of a variation of an embodiment of the present invention showing a unibody construction with three lumens.
Figure 10:
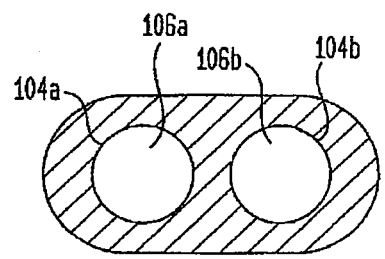
FIG. 10 is a cross-section view of an embodiment of the present invention showing an elliptical-shaped unibody construction.

FIG. 4 is a cross-section view of another embodiment showing opposed D-shaped lumens 104 where one lumen 104a is of a smaller size (e.g., smaller cross-sectional area) than the other lumen 104b. FIG. 5 is a cross-section view of an embodiment showing yet another unibody construction. FIG. 6 is a cross-section view of an embodiment showing individual, elliptical lumens inside an outer sheath 122. FIG. 7 is a cross-section view of an embodiment showing a unibody construction utilizing individual, elliptical lumens 104. FIG. 8 is a cross-section view of an embodiment showing three lumens 104, at least one of which (here, lumen 104c) having a different size and/or shape from at least one other lumen (here, lumens 104a, 104b). FIG. 9 is a cross-section view of a variation of an embodiment showing three lumens 104 having substantially the same size and shape. FIG. 10 is a cross-section view of another embodiment showing two elliptical-shaped lumens 104.

The lumens 104 can be made of any biocompatible material, including any material which allows the lumen tips 110, 114 of the lumens 104 to be flexible and facilitate hemodialysis. Furthermore, the lumen tip segment 114 can be made from a material different from a material of the cut lumen 104b. The different material can be one more or less flexible than the material of the cut lumen 104b. Using different materials for the lumen tip segment 114 and the cut lumen 104b can allow the catheter body 102 to be used more efficiently or to be used at all in an application where it would not be preferable or possible having material of the cut lumen 104b at the distal end 116b.

The distal extraction and return tip portions 110 of each lumen 104 include pathways 106 formed therein for the extraction or return of blood or other bodily fluids. The pathways 106 are preferably sized to allow the carrying of blood to and from a hemodialysis unit, although the pathways 106 can be any size and the catheter 100 can be used in any application. The distal extraction and return tip portions 110 can be the same length or, as discussed further below, can be different lengths.

An exemplary method of forming a split tip catheter is described with reference to FIGS. 11-26. Although described with reference to these figures (and related ones of FIGS. 1-10), this method (or a similar method) can be implemented to form any of the split tip catheter devices described herein.

Figure 11:
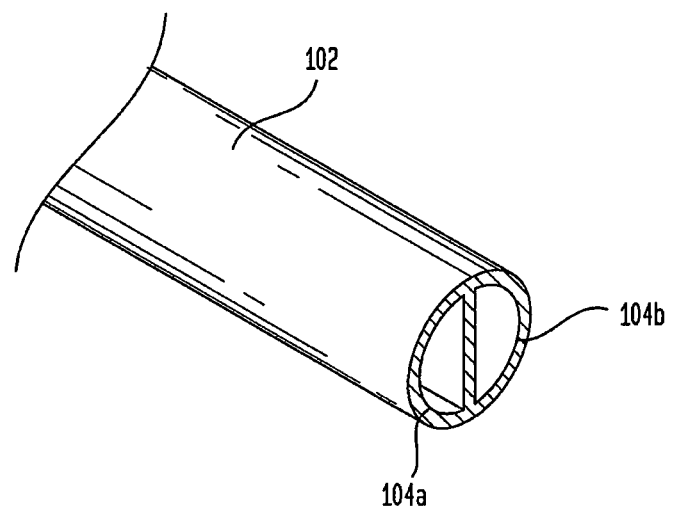
FIG. 11 is a schematic, perspective view of a catheter according to the present invention in an initial, pre-trimmed configuration.
Figure 12:
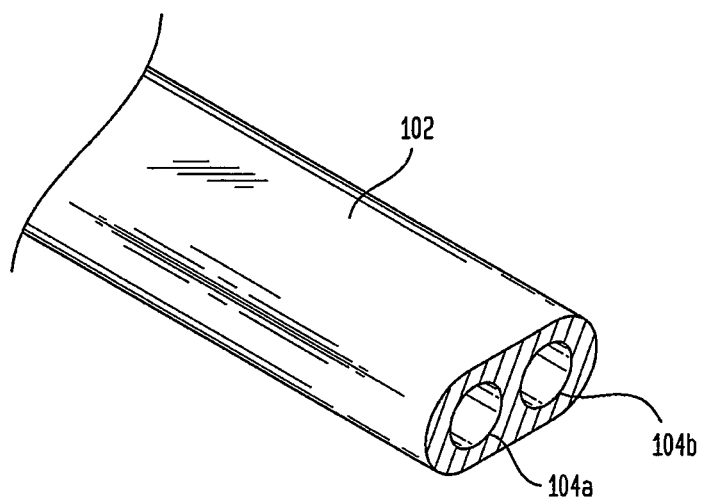
FIG. 12 is a schematic, perspective view of another catheter in an initial, pre-trimmed configuration.

FIG. 11 shows a circular catheter body 102 in an initial untrimmed configuration (e.g., without separate distal tip segments) having two "D-shaped" lumens 104a, 104b. FIG. 12 shows another, elliptical catheter body 102 with circular lumens 104a, 104b in an initial configuration (e.g., prior to trimming and joinder of a second distal lumen tip segment 114). Although the lumens 104 are shown having equal lengths in FIG. 12, the lumens 104 can have different lengths in this initial configuration.

Figure 13:
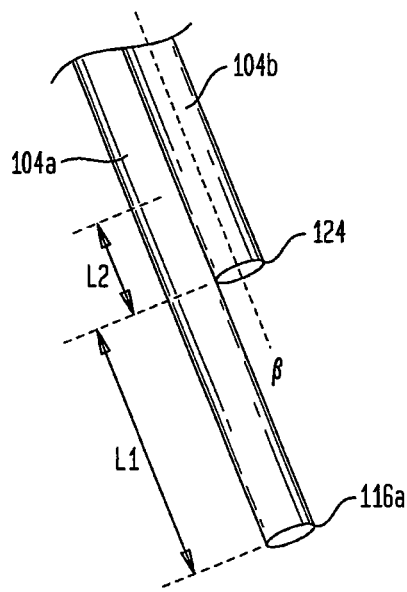
FIG. 13 is a schematic, perspective view of an embodiment of the present invention showing a trimmed catheter.

FIG. 13 shows the catheter body 102 in a trimmed configuration where a distal portion of the catheter body 102 has been removed, as compared to the initial configuration in FIG. 11 or 12. The catheter body 102 of FIG. 13 can also be formed by extending the lumens 104a, 104b in a staggered, step configuration such that one of the lumens 104a is extended longer than the other lumen 104b by a length L1. The lumens 104a, 104b can be aligned in this way while hot and can bond together in this formation as they cool. However formed, in this configuration, one of the lumens 104a (herein referred to as "the uncut lumen 104a") extends longitudinally beyond the other lumen 104b (herein referred to as "the cut lumen 104b") by a length L1. In an initial configuration such as in this embodiment where the lumens 104 initially have equal lengths, length L1 equals the amount of lumen trimmed from the cut lumen 104b. The length L1 can be in the range of about 1-3 inches, which is a preferable, but only an example, length of lumen to trim.

The sacrificed lumen 104a can be trimmed in a variety of ways. In a preferred example, one of the lumens 104b can be sliced (e.g., cut or scored) widthwise across its circumference at a location 124. Then a length L1 of the cut lumen 104b can be trimmed from the catheter body 102. When the length L1 of the cut lumen 104b has been removed, a septum between the cut lumen 104b and the uncut lumen 104a can thereby be at least partially exposed.

Referring again to FIG. 4 where one lumen 104a is smaller than the other lumen 104b, the larger lumen 104b is typically the arterial lumen because that is the one of the lumens 104 more prone to clogging in a hemodialysis setting, and a larger size pathway 106b can help reduce clogging. Truncation of the end portion according the invention typically involves sacrificing part of the larger lumen 104b and joining a new distal tip segment in its place. The catheter body 102 can again be split along an off-center longitudinal axis γ', thereby preserving most or all the septum 202, sacrificing part of lumen 104b (e.g., the part extending distally beyond the cut point 124). Following truncation, a new distal tip segment 114 (as shown in FIG. 1) can then be joined to the second lumen of the catheter body. The distal tip segment 114 can be similar in size and shape to the sacrificed lumen or can be different in size and/or shape.

In certain applications it can be preferable to sacrifice the smaller lumen 104a instead. In such instances, the truncation line can be moved to the other side of the septum 202.

Dimensions of the lumens 104a and 104b can vary between embodiments. In this example embodiment, dimensions allow the catheter body 102 to be used with standard hemodialysis equipment and lumen tip segments. Maximum width w2 of the smaller lumen pathway 106b is about 0.06 in. and maximum width w1 of the larger lumen pathway 106a is about 0.08 in. The septum 202 has a width w3 of about 0.02±0.002 in., while the lumens 104 have an exterior width w4 of about 0.022±0.003 in. Maximum height h2 of the smaller pathway 106a is about 0.14 in. and maximum height h1 of the larger pathway 106b is about 0.15 in.

Figure 14:
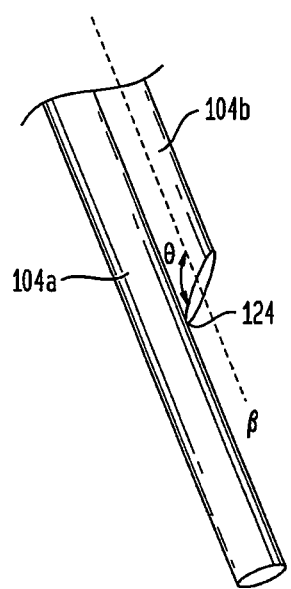
FIG. 14 is a schematic, perspective view of a variation of an embodiment of the present invention showing a trimmed catheter.

The cut distal end 124 of the cut lumen 104b can be trimmed in a perpendicular direction or a non-perpendicular direction with respect to a longitudinal axis β of the cut lumen 104b. FIG. 13 shows the cut distal end 124 trimmed in a perpendicular direction with respect to axis β. Alternatively, FIG. 14 shows the cut distal end 124 trimmed in a non-perpendicular direction with respect to axis β. The non-perpendicular direction can result in any non-zero angle θ between the cut distal end 124 and axis β. As shown in FIGS. 13 and 14, the distal extraction tip portion 110b of the blood extraction lumen 104b terminates proximal to the distal return tip portion 110a of the blood return lumen 104a. However, also including the lumen tip segment 114 attached to the distal tip return portion 110b as shown in FIG. 15, the two distal lumen tip segments 110 have the same length, although even including the lumen tip segment 114, one or the other of the lumen tips 110 can be longer than the other.

Figure 15:
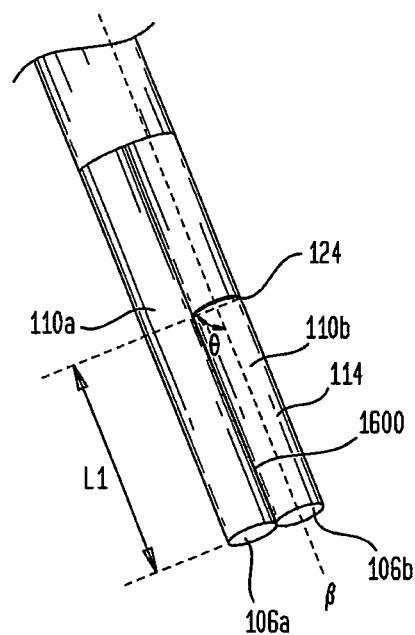
FIG. 15 is a schematic, perspective view of an embodiment of the present invention showing a lumen tube attached to a catheter.

With a distal portion of the catheter body 102 removed, the lumen tip segment 114 can be joined to the catheter body 102 as shown in FIG. 15. The lumen tip segment 114 has been joined to the lumen tip 110b of the cut lumen 104b at the cut distal end 124 such that the pathway of the cut lumen 104b is in communication with the pathway of the lumen tip segment 114, thereby forming a single pathway 106b through the cut lumen 104b and the lumen tip segment 114.

The lumen tip segment 114 can be attached to the catheter body 102 in a variety of ways. For example, the lumen tip segment 114 can be fused to the lumen tip 110b at the cut distal end 124. Any fusion technique can be used, e.g., thermal fusion where elements to be joined (here, the lumen tip segment 114 and the lumen tip 110b) are heated along any or all portions of their perimeters or other areas to a desired temperature and fused together by application of a desired force or by inserting one lumen tube over the other (e.g., with an overlap by about 1 cm) and allowing them to melt/cool together. In another example, the lumen tip segment 114 can be bonded to the lumen tip 110b at the cut distal end 124. Any bonding technique can be used, e.g., applying a bonding material such as an adhesive to one or more of the elements to be bonded and, if necessary, heating the bonding material to bond it to the elements. In some embodiments, the lumen tip segment 114 can be attached in such a way as to provide a gradual transition between the luminal walls of the catheter body 102 and the luminal walls of the lumen tip segment 114, for instance via the insertion of a mandrel and the application of heat.

Figure 16:
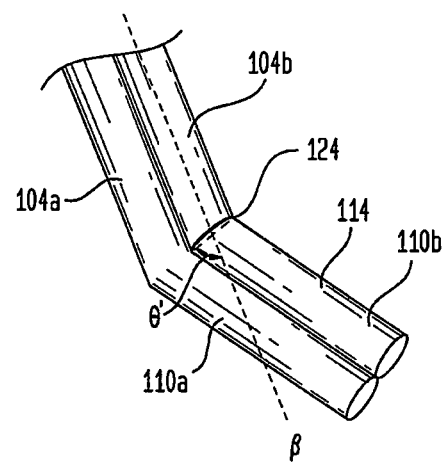
FIG. 16 is a schematic, perspective view of a variation of an embodiment of the present invention showing a lumen tube attached to a catheter.
Figure 17:
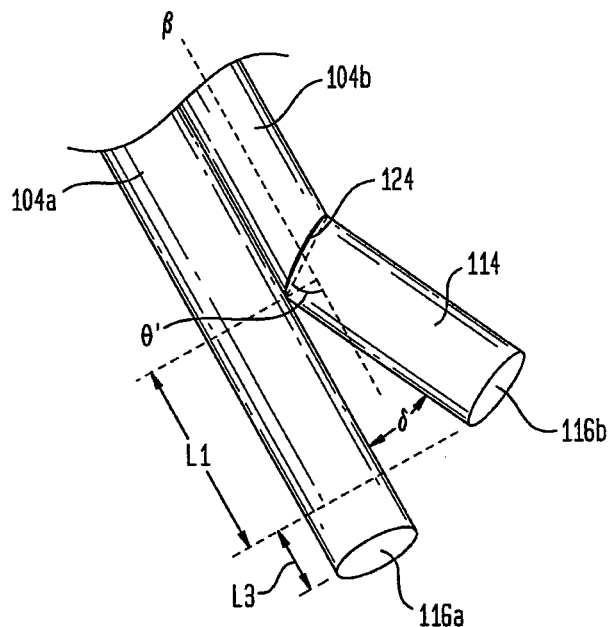
FIG. 17 is a schematic, perspective view of a variation of an embodiment of the present invention showing a lumen tube attached to a catheter.

The lumen tip segment 114 can be oriented at any angle with respect to the longitudinal axis β of the cut lumen 104b. Moreover, one or both of the lumen tip segment 114 and the lumen tip 110a can have a convex shape with respect to the other tip over at least some portion of its length. For example, the lumen tip segment 114 can be attached to the lumen tip 110b at a ninety degree angle θ' with respect to axis β as shown in FIG. 15. In such a configuration, the lumen tips 110 are separate but are substantially parallel to each other. FIG. 16 shows another embodiment where the lumen tips 110 are separate and substantially parallel to each other in an angled spit tip configuration, e.g., as described in U.S. Pat. No. 6,482,169, which is hereby incorporated by reference in its entirety. Alternatively, as shown in FIG. 17, the lumen tip segment 114 can be oriented to the cut lumen 104b at an angle θ' less than ninety degrees. In such a configuration, the lumens 104 are separate and diverge from each other at an angle σ. When the angle θ' is less than ninety degrees, it is typically in configurations where the cut distal end 124 has been trimmed in a non-perpendicular direction with respect to axis β, and the angle σ is formed when the lumen tip segment 114 is joined to the cut lumen 104b. However, the angle σ can be formed after the lumen tip segment 114 has been joined to the cut lumen tip 110b, e.g., by the application of heat. In another example, the design in FIG. 17 can be formed by first attaching the lumen tip segment 114 to the cut lumen tip 110b and then heating the lumens 104 to form the angle σ. Alternatively, the lumen tips 110 such as those in FIG. 17 can have an initial configuration where they are at the angle θ' with respect to axis β.

Figure 18:
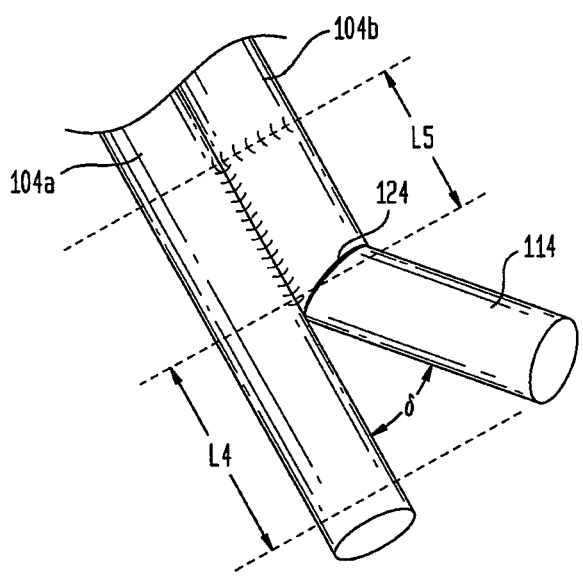
FIG. 18 is a schematic, perspective view of a variation of an embodiment of the present invention showing a lumen tube attached to a catheter, where the lumen tube is attached to at least a portion of the septum.
Figure 19:
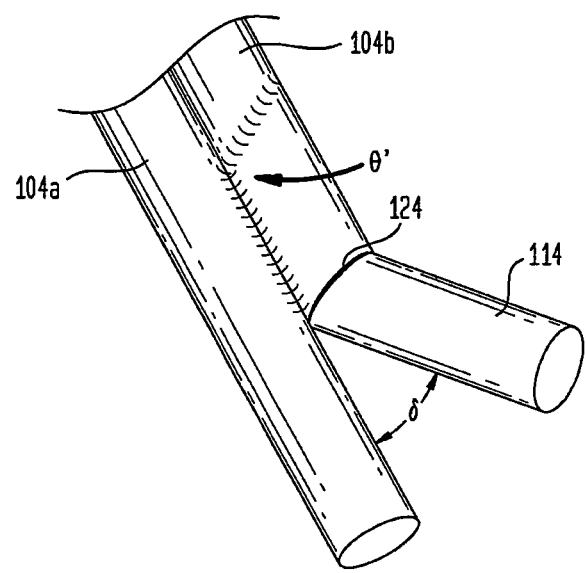
FIG. 19 is a schematic, perspective view of a variation of an embodiment of the present invention showing a lumen tube attached to a catheter, where the lumen tube is attached to at least a portion of the septum using an alternative method.

The apex of angle σ can be located either at the junction of the cut lumen 104b and the lumen tip segment 114, as shown in FIG. 17, or further toward the distal end of the catheter body 102. In the case that angle σ is further toward the distal end of the catheter body 102, the lumen tip segment 114 can be bonded to the septum along a length L5 of the uncut lumen 104a, as shown in FIG. 18. Alternatively, the lumen tip segment 114 can be bonded to the septum along the length L5 of uncut lumen 104a and attached to the cut lumen 104b at an angle θ', as shown in FIG. 19. Typically, in these or other embodiments, the lumen tip segment 114 can also be bonded along the circumference at the junction with the cut lumen 104b.

Whether substantially parallel or diverging from one another, the lumens 104 are separate (at least before application of any adhesive, discussed further below). FIG. 17 shows the lumens 104 separate for the length L1, and FIG. 18 shows the lumens 104 separate for the length L4. FIG. 17 also shows an embodiment where one of the lumens 104 is longer than the other, with the distal end 116a of the lumen tip 110a extending beyond the distal end 116b of the lumen tip segment 114 by a length L3.

Referring again to FIG. 15, the lumens 104 shown in this embodiment are substantially parallel and can be secured together with an adhesive 1600 for a length L1. Prior to the distal ends 116 of the catheter body 102 being inserted into a blood vessel, a full or partial portion of the lumen tips 110 of the lumens 104 can be joined to one another with the bioresorbable adhesive 1600. After insertion into the blood vessel, the bioresorbable adhesive 1600 facilitates separation of the lumen tips 110 of the lumens 104. As used herein, the term "bioresorbable" refers to materials that are biodegradable or biosoluble such that they degrade or break down by mechanical degradation upon interaction with a physiological environment into components that are metabolizable or excretable over a period of time.

The bioresorbable adhesive 1600 used to join the lumen tips 110 of the lumens 104 to one another can be a composition selected from the group of polymers consisting of polylactides, polyglycolides, polylactones, polyorthoesters, polyanhydrides, and copolymers and combinations thereof. In general, bioresorbable adhesives have bonding elements and degradable elements. The degradable elements can have the components of polylactide, polyglycolide and polylactones (polycaprolactone). The bonding elements can have hydrogen bonding strength (polyvinyl alcohol, polysaccharides) or can be able to polymerize as a single component (cyanoacrylates) or as two components (epoxy compound plus amino compounds, or radical (light) initiators of acrylate compounds).

Proteins, sugars, and starch can also be used as an adhesive. By way of non-limiting example, antithrombotic agents such as heparin and hirudin, citrate, antithrombin-heparin complex, and albumin heparin complex as well as anti-infective agents such as chlorohexidine, silver, antibiotics, and antiseptic agents may be added to the adhesive.

In an embodiment of the present invention, polymers which can be useful include polyurethane, generally described as a copolymer of polyethylene glycol with polylactide or polyglycolide end capped with methacrylates. Another embodiment can include a two component composition, one component preferably including a low molecular weight polyurethane end capped with methacrylates, and the other component preferably including polylactide, polyglycolide, or polycaprolactone end capped with methacrylate.

In another embodiment of the present invention, one or more components can be used from styrene, methyl methacrylate, methyl acrylate, ethylene dimethacrylate, ethylene diacrylate, acrylamide, diurethane dimethacrylate, polyisoprenegraft-maleic acid monomethyl ester, azobis (cyanovaleric acid), azobiscyclohexanecarbonitrile, azobisisobutyronitrile, benzoyl peroxide, iron (II) sulfate, polyvinyl alcohol, dextran, polysaccharide, epichlorohydrin, ethylenediamine, diaminocyclohexane, diamino propane, copolymers with polylactide and polyethylene oxide as the blocks and acrylate, methacrylate as the end groups, cyanoacrylates, ethyl-2cyanoacrylate, propyl-2-cyanoacrylates, pentyl-2-cyanoacrylate, hexyl-2-cyanoacrylate, and octyl-2-cyanoacrylate, ammonium persulfate and/or polyethylene glycol methacrylate when water, organic solvent such as dichloromethane, chloroform, tetrahydrofuran, acetone, petroleum ether, acetyl acetate, dimethylformamide, or the mixture thereof, is combined with the aforementioned solvents.

As shown in FIG. 15, the bioresorbable adhesive 1600 can be applied along a facing surface of either, or both, the lumen tips 110 of the lumens 104 to facilitate the joining of the lumen tips 110 along their longitudinal lengths prior to insertion of the distal ends 116 of the catheter body 102 into a blood vessel. (As used throughout, "the catheter body 102" and its components refers to the various embodiments of the present invention.) FIG. 15 shows the bioresorbable adhesive 1600 applied along a longitudinal length L1. However, the bioresorbable adhesive 1600 need not be applied along the entire length of the facing surfaces of each lumen 104 but is preferably applied such that the adhesive 1600 facilitates the joining of the lumen tips 110 of the lumens 104 prior to insertion into a blood vessel and allows the lumen tips 110 of the lumens 104 to separate after insertion. Furthermore, the bioresorbable adhesive 1600 can be applied along more than length L1 if, for example, the lumens 104 were separated an additional length L2, in which case the adhesive 1600 can be applied along a length equal to L1+L2.

Figure 20:
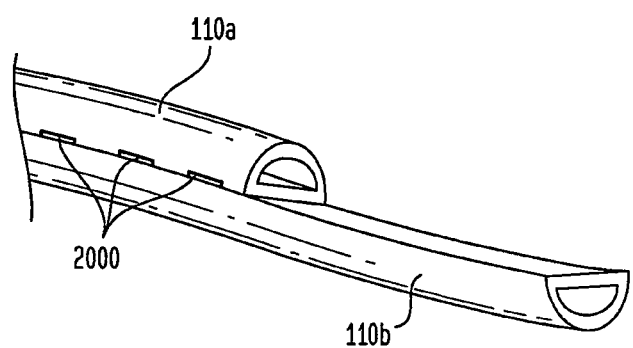
FIG. 20 is a schematic, perspective view of an embodiment of the present invention showing an adhesive application.

In an embodiment shown in FIG. 20, bioresorbable adhesive can be applied to facing surfaces of the lumen tips 110 of the lumens 104 as discrete spots or regions 2000. (Assume in this example that the lumen tip segment 114 has already been attached to the cut lumen tip 110b.) The spots 2000 of the bioresorbable adhesive can be applied continuously along the entire longitudinal length of the lumen tips 110 of the lumens 104 or selectively in an assortment of areas thereof. Preferably, the bioresorbable adhesive is applied such that the spots 2000 of adhesive facilitate the joining of the lumen tips 110 of the lumens 104 prior to insertion into a blood vessel and allow the distal extraction and return tips 110 of the lumens 104 to separate after insertion. The spots 2000 of bioresorbable adhesive can vary in number, size, and distance from one another in order to facilitate the joining and/or disjoining of the lumen tips 110 of the lumens 104.

In the embodiments described herein, the bioresorbable adhesive preferably dissolves after insertion into a blood vessel to provide separation of the lumen tips 110 of the lumens 104 in a time period ranging from one minute to one hour (but as long as several days or longer). This range can be controlled by using different compositions of the bioresorbable adhesive as well as by the amount of adhesive applied to join the lumen tips 110 of the lumens 104 together.

In another embodiment with opposed distal fluid openings 112 (further described below), the bioresorbable adhesive can be water soluble such that the introduction of saline or similar type fluid will effectuate the separation of the lumen tips 110 of the lumens 104. In this instance, the bioresorbable adhesive will not dissolve until a time after the introduction of the soluble solution into the lumens 104.

Figure 21:
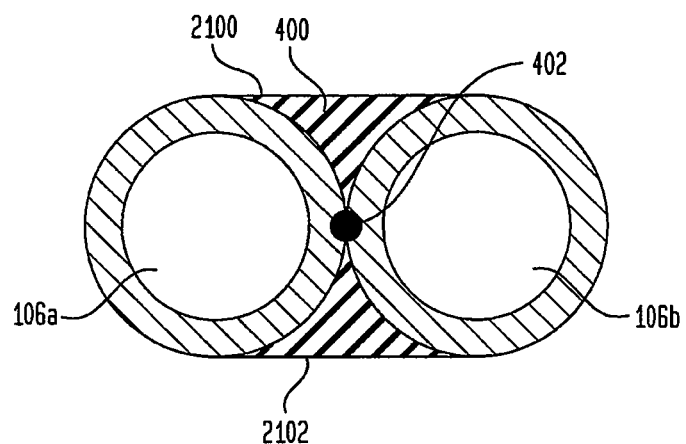
FIG. 21 is a distal cross-sectional view of another embodiment of the present invention showing alternative adhesive disposition.
Figure 22:
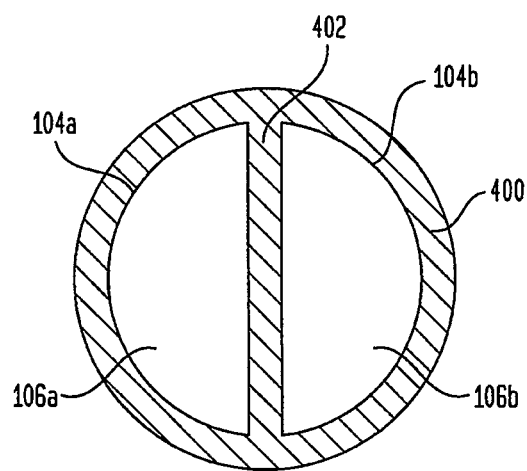
FIG. 22 is a distal cross-sectional view of yet another adhesive design.

FIGS. 21-22 show cross-sections of the lumen tips 110 of the lumens 104 detailing alternate embodiments of the bioresorbable adhesive application. FIGS. 21 and 22 show the bioresorbable adhesive 400 applied at a contact point 402 of the facing surfaces of the lumens 104. FIG. 21 shows one embodiment of an application of the bioresorbable adhesive 400 such that the adhesive 400, as applied, joins non-contacting surfaces 2100, 2102 of the lumen tips 110 of the lumens 104. FIG. 22 shows a variation on the embodiment shown in FIG. 21 where the bioresorbable adhesive 400 surrounds the lumen tips 110 of the lumens 104 forming a continuous cross-section of adhesive coating notwithstanding the lumen tips 110 of the lumens 104 extending therethrough. As stated above, the bioresorbable adhesive 400 need not be applied along the entire length of the lumen tips 110 of the lumens 104 but is preferably applied such that the adhesive 400 facilitates the joining of the distal extraction and return tip portions 110 of the blood extraction and blood return lumens 104 prior to insertion into a blood vessel and allows the lumen tips 110 of the lumens 104 to separate after insertion. Furthermore, the lumen tips 110 can have different coatings from one another and/or different from a coating on the catheter body 102.

Figure 23:
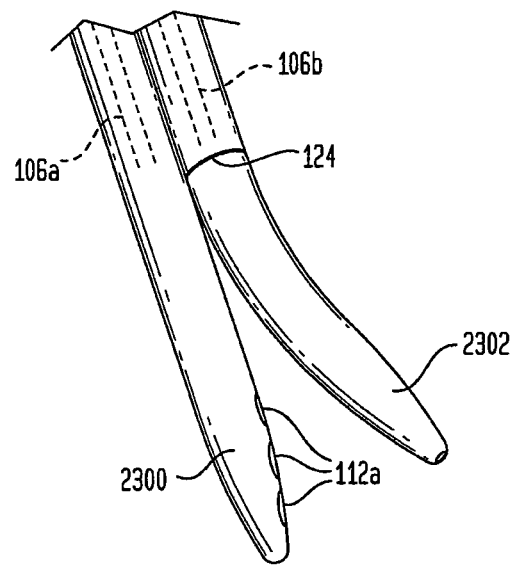
FIG. 23 is a schematic, perspective view of an embodiment of the present invention showing fluid openings in the distal tip.

FIG. 23 shows another embodiment where distal fluid openings (also called fluid passage holes) 112a are formed in the lumen tip 110a of the lumen 104a. It should be understood from the drawings that in the embodiment shown, the distal fluid openings 112a can either be in addition to, or in place of, the pathway opening located at the distal end 116a of the lumen 104a. Furthermore, the cut lumen 104b can have distal fluid openings 112b similar to those described here, whereby the fluid openings 112b would typically be included in the lumen tip segment 114 attached to the cut lumen tip 110b or subsequently formed in the lumen tip segment 114 after its attachment to the cut lumen tip 110b.

The distal fluid openings 112a can be any shape and size and can be located in a variety of places on the lumen 104a. FIG. 23 shows the distal fluid openings 112a located on facing (contacting) surface 2300 of the lumen tip 110a of the lumen 104a. In this embodiment, the distal fluid openings 112a can be filled or covered with fluid activated bioresorbable adhesive and joined to the other lumen 104b along its facing surface 2302. After insertion of the catheter body 102 into a blood vessel, saline or similar type fluid can be introduced into the lumen 104a at its proximal end 118 such that the fluid travels through the lumen 104a to the distal fluid openings 112a and dissolves the fluid activated bioresorbable adhesive thereby separating the lumen tips 110 along their longitudinal length to, e.g., facilitate hemodialysis. Bioresorbable adhesive can also be applied to the contact surfaces 2300, 2302 of each lumen 104 as previously described above in addition to the distal fluid openings 112a being filled or covered with fluid activated bioresorbable adhesive.

Figure 24:
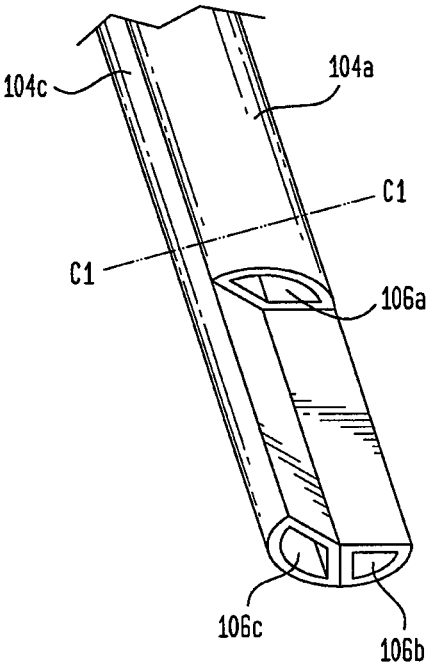
FIG. 24 is a cross-section view of a variation of an embodiment of the present invention showing a trimmed catheter.
Figure 25:
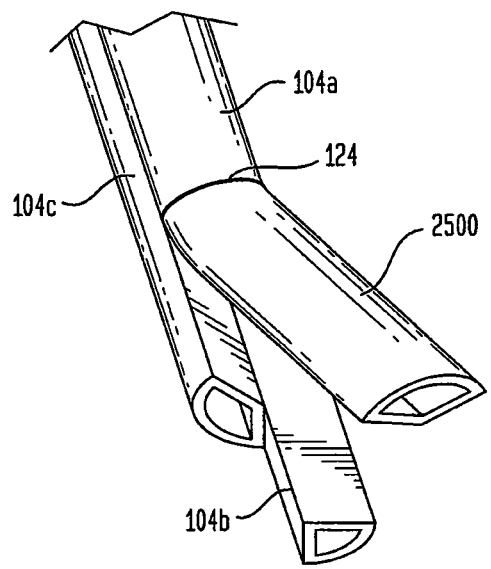
FIG. 25 is a cross-section view of a variation of an embodiment of the present invention showing another trimmed catheter.

FIGS. 1-7 and 11-23 illustrate double lumen configurations, but the split tip catheter devices and methods described herein can apply to any multi-lumen configuration. For example, FIG. 24 shows an embodiment of a catheter body 2400 having three lumens 104a, 104b, 104c, each having respective pathways 106a, 106b, 106c. The catheter body 2400 can have any c1-c1 cross-sectional configuration, and in this example is shown having the one in FIG. 9. One of the lumens 104a in this example has been split from the other lumens 104b, 104c, and the lumen 104a been trimmed. FIG. 25 shows the catheter body 2400 of FIG. 24 where a second lumen 104c has been split from the other lumen 104b and trimmed. A lumen tip segment 2500 has been attached to the first trimmed lumen 104a, and another lumen tip segment can be attached to the second trimmed lumen 104c.

Figure 26:
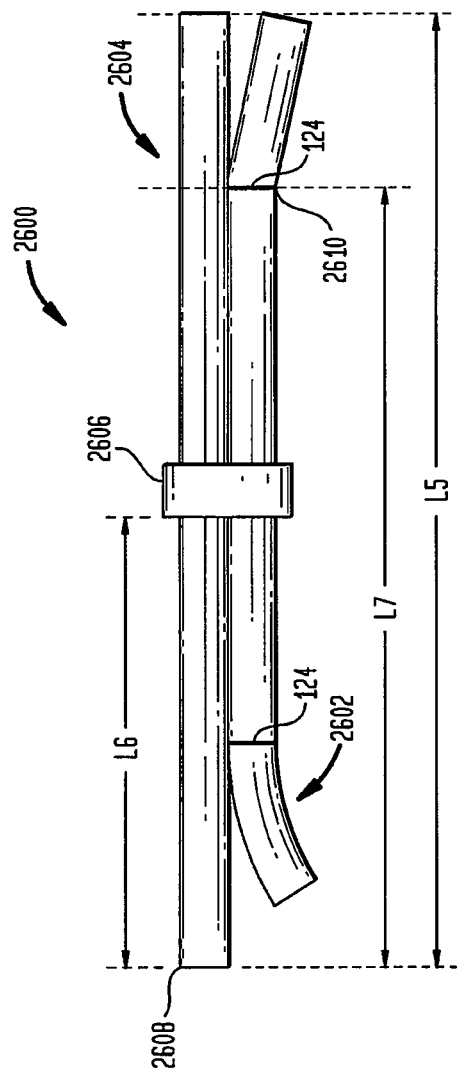
FIG. 26 is a schematic side view of a catheter according to the present invention.

The above embodiments describe a split distal end of a catheter, but in addition to or instead of splitting the distal end, the proximal end can also be formed in a split tip configuration in any way described above with respect to the distal end (e.g., in a double split-tip or "double-Y" configuration). Such a configuration can be useful in retrograde or reverse insertions where the catheter body is passed through a subcutaneous tunnel from venotomy site to the remote exit location. After tunneling the catheter, fluid couplings or other attachments can be disposed to the proximal end of the lumens. FIG. 26 shows an embodiment of a catheter body 2600 having a split distal end 2602 and a split proximal end 2604. A cuff 2606 can be attached to any location on the catheter body 2600 to enhance tissue ingrowth. The catheter can have any dimensions, but only as an example, the catheter body 2600 can have a length L5 of about 38 cm, a length L6 between a distal most end 2608 of the distal end 2602 and the cuff 2606 can be about 23 cm, and a length L7 between the distal most end 2608 and a cut proximal end 2610 can be about 28 cm.

Other embodiments are within the scope of the following claims.

All publications, patent documents and other information sources identified in this application are hereby incorporated by reference.

What is claimed is:

1. A method of forming a split tip catheter, comprising:
   providing an elongate catheter body comprising at least a first lumen and a second lumen extending longitudinally through the catheter body;
   removing a distal portion of the catheter body to form a first lumen tip segment such that the first lumen extends longitudinally beyond the second lumen; and
   joining a second lumen tip segment to the catheter body in communication with the second lumen.

2. The method of claim 1, wherein the step of joining a second lumen tip segment further comprises fusing the second lumen tip segment to the catheter body.

3. The method of claim 1, wherein the step of joining a second lumen tip segment further comprises orienting the second lumen tip segment such that the first and second lumen tip segments are separate but substantially parallel to each other.

4. The method of claim 1, wherein the step of joining a second lumen tip segment further comprises orienting the second lumen tip segment such that the first and second lumen tip segments are separate and diverge from each other at an angle.

5. The method of claim 1, further comprising forming an angle between the first and second lumen tip segments after the second lumen tip segment is joined to the catheter body.

6. The method of claim 5, wherein at least one of the first and second lumen tip segments forms a compound angle or a curve.

7. The method of claim 5, further comprising forming an angle between the first and second lumen tip segments by applying heat.

8. The method of claim 1, wherein the step of removing a portion of the catheter body further comprises partially slicing the catheter body in a non-perpendicular direction with respect to a longitudinal axis of the catheter body.

9. The method of claim 1, further comprising forming fluid passage holes in a side of at least one of the lumen tip segments.

10. The method of claim 1, further comprising securing the first and second lumen tip segments together with a bioresorbable adhesive.

11. The method of claim 1, further comprising coating at least a portion of the first and second lumen tip segments with at least one agent selected from the group of antithrombotic agents, antibacterial agents, anti-inflammatory agents.

12. A method of forming a split tip catheter, comprising:
providing a multi-lumen catheter body having at least a first lumen and a second lumen extending therethrough;
partially truncating the multi-lumen catheter body such that a first distal lumen tube is formed to longitudinally extend a distal end of the first lumen of the catheter further than a distal end of at least the second lumen of the catheter; and
attaching a second distal lumen tube to a truncated end of the catheter such that a pathway separate from the first distal lumen tube is formed in fluid communication with the second lumen of the catheter.

13. The method of claim 12, further comprising forming a non-zero angle between the first and second distal lumen tubes.

14. The method of claim 13, wherein the non-zero angle varies over at least a portion of the first and second distal lumen tubes.

15. The method of claim 12, further comprising forming a zero angle between the first and second distal lumen tubes.

16. The method of claim 12, further comprising forming a non-zero angle between at least one distal lumen tube and a longitudinal axis of the catheter body.

17. The method of claim 12, further comprising:
further truncating the distal end of the catheter body to isolate a third lumen; and
attaching a third distal lumen tube to the catheter body.

18. The method of claim 12, wherein a septum separates the first lumen and second lumen and the step of partially truncating the catheter body further comprises truncating the body at a truncation point such that at least a portion of the septum is retained by the first distal lumen tube.

19. The method of claim 18, wherein the step of attaching the second distal lumen tube further comprises attaching the second distal lumen tube at least partially to the septum of the first distal lumen tube.

20. The method of claim 12, wherein the step of attaching the second distal lumen tube further comprises attaching the second distal lumen tube that has a different shape than the first or second lumen.

21. The method of claim 12, wherein the step of attaching the second distal lumen tube further comprises attaching the second distal lumen tube such that luminal walls of the catheter body gradually transition to luminal walls of the second distal lumen tube.

22. A method of forming a split tip catheter, comprising:
providing a multi-lumen catheter body having at least a first lumen and a second lumen extending therethrough;
partially truncating the multi-lumen catheter body such that a first distal lumen tube is formed to longitudinally extend a distal end of the first lumen of the catheter further than a distal end of at least the second lumen of the catheter;
attaching a second distal lumen tube to a truncated end of the catheter such that a pathway separate from the first distal lumen tube is formed in fluid communication with the second lumen of the catheter; and
forming a second split end portion by:
partially truncating the multi-lumen catheter body at a proximal end of the catheter body such that a first proximal lumen tube is formed to longitudinally extend the first lumen of the catheter further than at least a second proximal lumen of the catheter, and
attaching a second proximal lumen tube to the truncated proximal end of the catheter such that a pathway separate from the first proximal lumen tube is formed in fluid communication with the second lumen of the catheter.

23. A method of forming a split tip catheter, comprising:
splitting a distal end of a catheter body having two or more lumens at a septum dividing two of the lumens to isolate a first distal end tube, truncating the catheter body such that the first distal end tube is formed and the first distal end tube surrounds a first lumen having a length that extends beyond a truncation point; and
attaching a second distal end tube to the catheter body in fluid communication with a second lumen of the body.

24. A method of forming a split tip catheter, comprising:
providing a multi-lumen catheter body having at least a first lumen and a second lumen extending therethrough;
partially truncating the multi-lumen catheter body such that a first distal lumen tube is formed to longitudinally extend the first lumen of the catheter further than at least the second lumen of the catheter; and
attaching a second lumen tube to a truncated end of the catheter such that a pathway separate from the first distal lumen tube is formed in fluid communication with the second lumen of the catheter wherein the second lumen has a different shape than the first lumen.

* * * * *